(12) United States Patent
Evans et al.

(10) Patent No.: US 6,193,653 B1
(45) Date of Patent: Feb. 27, 2001

(54) METHODS AND DEVICES FOR VISUALIZING, DISSECTING AND HARVESTING VESSELS AND THE LIKE

(75) Inventors: David K. Evans, Fishers, IN (US); Ronald J. Brinkerhoff, New Richmond, OH (US); Hal H. Katz, West Chester, OH (US); William J. Kraimer, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 0 days.

(21) Appl. No.: 09/245,946

(22) Filed: Feb. 5, 1999

Related U.S. Application Data

(60) Provisional application No. 60/073,890, filed on Feb. 6, 1998.

(51) Int. Cl.[7] .................................................. A61M 17/00
(52) U.S. Cl. ........................... 600/210; 606/159; 606/170; 606/190
(58) Field of Search ............................... 606/1, 108, 159, 606/170, 171, 180, 190, 191; 600/210, 212

(56) References Cited

U.S. PATENT DOCUMENTS

| 1,246,338 | 11/1917 | Smit . |
| 2,831,480 | 4/1958 | Milano . |
| 2,840,070 | 6/1958 | Tofflemire . |

(List continued on next page.)

FOREIGN PATENT DOCUMENTS

| 0 642 764 A1 | 3/1995 | (EP) . |
| 0761172A2 | 7/1996 | (EP) . |
| 1371689 | 2/1988 | (SU) . |
| WO 94/09701 | 11/1994 | (WO) . |
| WO 95/10982 | 4/1995 | (WO) . |

OTHER PUBLICATIONS

"Endoscopic Subfascial Discission of Perforating Veins", (G. Hauer et al., Surg Endosc (1988) 2: 5–12).
"A quick and atraumatic method of autologous vein harvesting using the subcutaneous extraluminal dissector", (W.R. Dimitri et al., J. Cardiovasc Surg, 1987; 28:103–11).
"Long Sapnenous Vein Harvesting", (W. Meldrum–Hanna et al., Aust. N.Z. J. Surg 1986, 56, 923–924).
"Vein Harvest", Alan B. Lumsden & Felmont F. Eaves, III, Endoscopic Plastic Surgery (Quality Medical Publishing, Inc., 1995), pp 535–543.
"Endoscopic Plastic Surgery", Snowden–Pencer, Inc. (1993 Brochure).
"Instrument for Endoscopic Removal of the Great Saphenous Vein" Endo World 1997, (includes unverified English Translation pp 2–3).
Endopath Subscu–Refractor, Subcutaneous Endoscope-–Holding Retractor, product brochure, 1997.
Endsaph vein harvest system, Setting New Standards in Minimally Invasive Harvesting of the saphenous Vein, General Surgical Innovations product brochure, 93–0026–01.A.

*Primary Examiner*—Michael Buiz
*Assistant Examiner*—William Lewis
(74) *Attorney, Agent, or Firm*—Woodard, Emhardt, Naughton, Moriarty & McNett

(57) ABSTRACT

A device useful in minimally-invasive procedures involving the visualization, dissection and/or harvesting of vessels in the body includes a shaft having a handle mounted on one end and a dissecting tip on the other end. The dissecting tip optionally includes a light source for directing light transverse of the tip and structures to retain the tip in position adjacent the vessel as the tip is advanced along the vessel. Also disclosed are associated methods for transilluminating a vessel, dissecting the vessel from surrounding tissue, and transecting the vessel and side branches and removing the vessel from the body.

64 Claims, 18 Drawing Sheets

U.S. PATENT DOCUMENTS

| | | |
|---|---|---|
| 2,944,552 | 7/1960 | Cannon . |
| 3,651,800 | 3/1972 | Wilbanks . |
| 4,232,660 | 11/1980 | Coles . |
| 4,793,346 | 12/1988 | Mindich . |
| 5,352,219 | 10/1994 | Reddy . |
| 5,373,840 | 12/1994 | Knighton . |
| 5,448,990 | 9/1995 | De Faria-Correa . |
| 5,591,183 | 1/1997 | Chin . |
| 5,601,581 | 2/1997 | Fogarty et al. . |
| 5,607,441 | 3/1997 | Sierocuk et al. . |
| 5,667,480 | 9/1997 | Knight . |

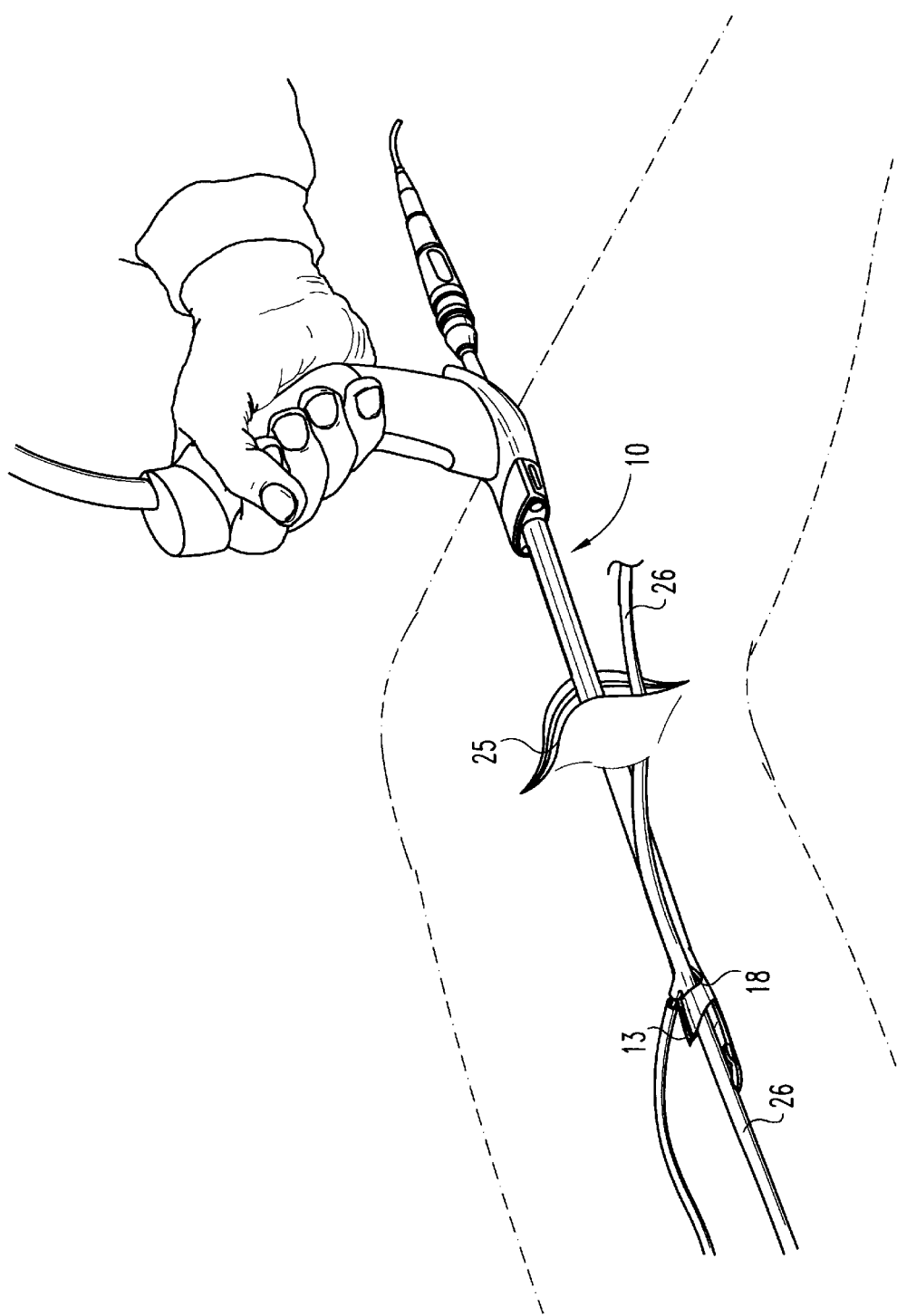

METHODS AND DEVICES FOR VISUALIZING, DISSECTING AND HARVESTING VESSELS AND THE LIKE

This application claim benefit to Provisional application 60/073,890 and filing date Feb. 6, 1998.

BACKGROUND OF THE INVENTION

1. Field of the Invention

The present invention relates to new, efficient, minimally-invasive methods and devices for visualizing, dissecting and/or harvesting blood vessels and the like.

2. Description of the Prior Art

In many cases it is desirable to visualize a section of a blood vessel of the body, and in some instances to remove the vessel, possibly as a replacement for a defective or diseased portion of a blood vessel in another part of the body. For example, damage to or occlusion of coronary arteries is frequently remedied by using a vessel from another location as graft material in a coronary artery bypass grafting procedure. The saphenous vein has been commonly used as the grafting material in this procedure.

Conventional methods of removing a vessel from a patient involve an open surgical procedure whereby an incision is made along the length of the vessel desired to be harvested. For example, when harvesting the saphenous vein, a large incision is made along the interior length of the patient's leg (from groin to knee, knee to ankle or ankle to groin). This procedure can result in significant post-operative pain and wound site complications such as hematoma, wound infection and delayed healing. Cosmetically undesirable scars remain behind as well.

Efforts to overcome the drawbacks of the conventional methods have led to the development of several minimally invasive methods. For example, Mindich discloses the use of an elongated plastic tube having at least one knife blade mounted on its distal end to harvest a section of vein. U.S. Pat. No. 4,793,346 (1988). The knife blade can be heated by supplying current through electrical conductors extending the length of the tube. The disclosed process comprises making two different incisions in the body of a patient, one at either end of the desired vein. The vein is then severed at each end, one end of the vein is inserted into the tube, and the tube is advanced along the length of the vein. The rotating knife blades sever any side branches that are present and cauterize the severed ends.

Several endoscopic procedures have attempted to improve upon the minimally invasive vessel harvesting procedures. For example, Knighton describes the use of an endoscope having a lumen extending longitudinally along its body to harvest a section of a blood vessel from a patient through an incision. U.S. Pat. No. 5,378,840 (1994). The blood vessel is transected at its proximal end, a grasping instrument is inserted through the lumen of the endoscope in order to hold the proximal end of the vessel in place, and the endoscope is advanced along the length of the vessel until the desired length of vessel is obtained. When branch points are reached, they are ligated and cut with a ligation-cutting tool introduced through the lumen of the endoscope. The blood vessel is then severed at its distal end and the vessel, within the lumen of the endoscope, is removed from the body.

When used to harvest the saphenous vein, the side branches of the vein limit the maneuverability of the endoscope since the outer edge of the endoscope body is prevented from advancing along the trunk of the saphenous vein until the encountered side branches are ligated and transected. Moreover, this method may require several hands and thus more than one individual. One hand is required to hold and maintain the endoscope in position, a second hand is required to hold the free end of the transected vessel with a grasper, and a third hand is required to dissect connective tissue away from the vessel.

Fogarty et al. teach a method and device for blood vessel harvesting utilizing an endoscope and a side-hooked wire. U.S. Pat. No. 5,601,581 (1997). A working space is first created along, for example, the saphenous vein by making small incisions near the knee and groin, inserting a blunt tunneling tool into one incision, and pushing the tool towards the other incision. The tunnel can be further expanded with a balloon dissector. The incisions are sealed and a gas such as carbon dioxide is introduced into the tunnel. A side-hooked wire is then introduced and is used to pry the vein from its connective tissue. Side branches are detected when resistance is felt while pulling the hooked wire. The side branches are then visualized with the endoscope and the branches are ligated and severed.

Knight teaches the use of an optical dissector and an optical retractor to endoscopically harvest a blood vessel. U.S. Pat. No. 5,667,480 (1997). The optical dissector comprises a shaft with a lumen extending longitudinally along its length and containing an endoscope. The end of the dissector is comprised of a spoon-shaped working head that can bluntly dissect subcutaneous tissue. The retractor also has a spoon-shaped working head that allows instrumentation such as dissectors, ligators and cutting devices to be inserted into the working space.

In harvesting a saphenous vein using this procedure, a small incision is made in the patient's leg near the vessel. The optical dissector is introduced through the incision to dissect tissue away from the superior surface of the vessel. The optical retractor is then used to retract dissected tissue away from the vessel and allows for passage of a vessel dissector to dissect connective tissue from the vein. The course of both the dissection and the retraction is visualized with the attached endoscope. Side branches are dissected, ligated and transected as necessary and the vessel is removed with endoscopic graspers through the incision.

Although this procedure is minimally invasive, there is room for improvement. Significantly, a longer period of time is required to complete the procedure compared to other techniques. For example, whereas the open surgical technique requires approximately 35 minutes to perform, this endovascular harvesting technique may require as much as 1.5 hours for inexperienced individuals, with the average time being 40–60 minutes. Any increased procedure time could also increase the likelihood of infection. Further, this method can require a significant amount of training time (e.g., five to ten cases) to adjust the surgeon's hand-eye coordination in using an endoscope. Trauma to the patient is more likely to occur due to the difficulty in developing this skill. Finally, this method requires a significant amount of space in the operating room due to the number of assistants that are needed as well as the presence of the bulky videoscopic equipment. All of these factors add to the increased risk to the patient and increased costs associated with this procedure.

There has therefore remained a need for a cost effective technique for harvesting a blood vessel that is minimally invasive, reduces the likelihood of damage to the vessel to be harvested, allows for more direct monitoring of the vessel to be harvested, uses space efficiently, requires less training, and reduces the possibility of injury to the patient and concomitant patient morbidity.

SUMMARY OF THE INVENTION

Briefly describing one aspect of the present invention, there is provided a device useful for visualizing, dissecting and/or harvesting a vessel or similar structure of the body. The device includes a shaft having a handle attached to the proximal end and a dissecting tip attached to the distal end. In one embodiment the tip includes a light source for directing light laterally of the tip. In a method for visualizing a vessel, the tip and light source are positioned posterior of the vessel and the light transmitted past the vessel and through the skin permits visualization of the vessel from outside of the body. In another aspect, the dissecting tip includes various retaining structures for retaining the tip in position adjacent to the vessel as the tip is advanced along the vessel. The tip and particularly the retaining structures may also be configured to have edges and surfaces which facilitate dissection of the vessel from the surrounding tissue and transection of side branches of the vessel.

The invention also provides methods utilizing the foregoing devices to dissect a vessel or the like from associated tissue, and optionally to remove the vessel from the body. Such methods include making an incision in the body adjacent the vessel, inserting the dissection device into the body and positioning the vessel within one or more provided retaining structures, and advancing the device along the vessel to dissect the vessel from surrounding tissue. In addition, the methods may further include transecting the vessel at selected proximal and distal locations and thereafter removing the vessel from the body.

It is an object of the present invention to provide methods and devices for minimally-invasive surgical procedures involving the visualization, dissection and/or harvesting of vessels.

It is another object of the invention to provide such methods and devices which are simple and inexpensive in construction, easily used with reduced training requirements, and provide superior operative results for patients.

A further object is to provide devices and methods useful for harvesting vessels and the like, for example the saphenous vein, in a quicker and less traumatic fashion, with less equipment and therefore less cost, and which particularly includes minimal skin incisions which are more readily closed and heal more quickly with less pain and fewer complications.

Further objects and advantages of the present invention will be apparent from the following description of the preferred embodiments.

BRIEF DESCRIPTION OF THE DRAWINGS

FIG. 30 is a perspective view showing the insertion of the dissecting device beyond a transected side branch.

DESCRIPTION OF THE PREFERRED EMBODIMENT

Figure 1:
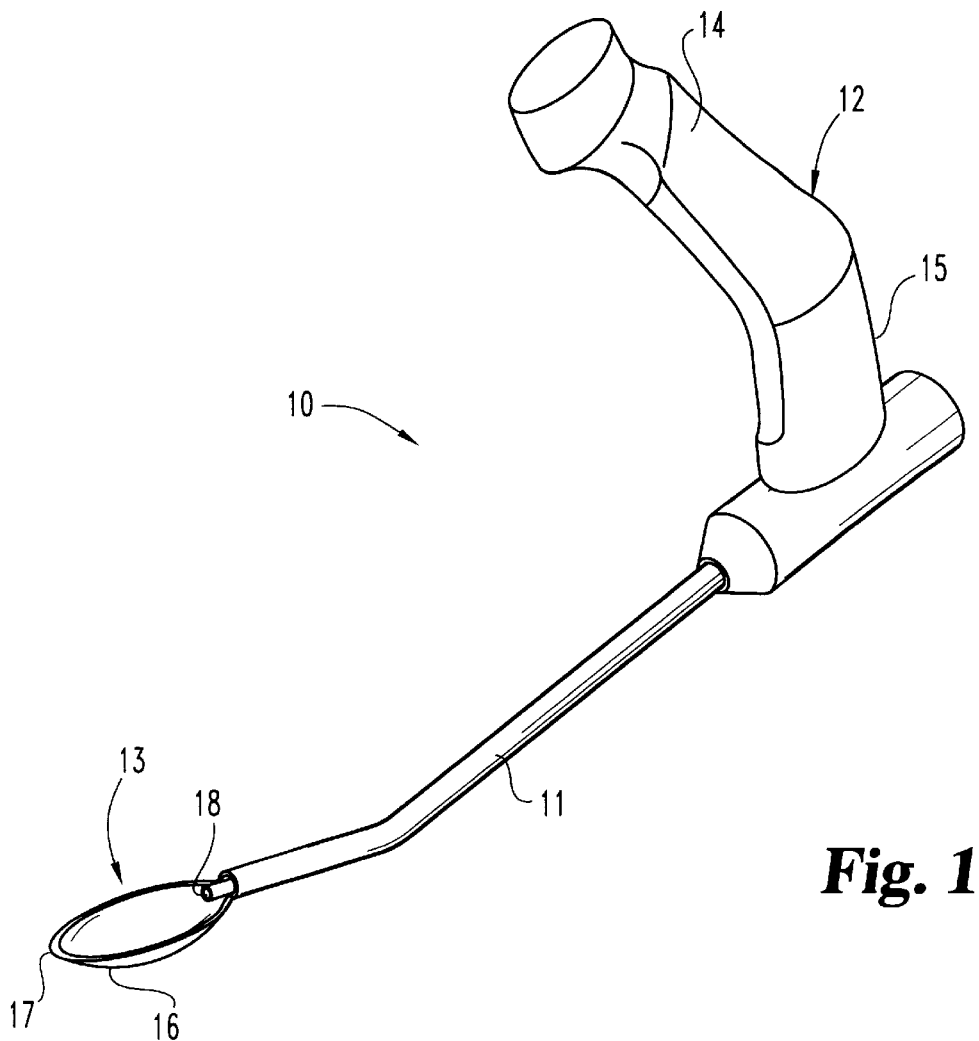
FIG. 1 is a perspective view of a device constructed in accordance with the present invention.

For the purposes of promoting an understanding of the principles of the invention, reference will now be made to the embodiment illustrated in the drawings and specific language will be used to describe the same. It will nevertheless be understood that no limitation of the scope of the invention is thereby intended, such alterations and further modifications in the illustrated device, and such further applications of the principles of the invention as illustrated therein being contemplated as would normally occur to one skilled in the art to which the invention relates.

The present invention provides instrumentation useful for minimally-invasive procedures involving the visualization, dissection and/or harvesting of vessels and the like. The devices and methods are described by way of example in regard to use with blood vessels, although use also applies with other elongated structures, such as tendons. The basic device includes a shaft having a handle attached to the proximal end and a dissecting tip attached to the distal end. The handle is configured to facilitate manipulation of the device for its various intended uses.

The dissecting tip may assume a variety of designs depending on the use. For example, the inclusion of a light source enables visualization of a vessel through the skin of the body. Positioning the light source posterior of the vessel provides transillumination of the vessel as the light passes the vessel and associated tissue and can be viewed from exterior of the body through the skin. In addition, particular retaining structures may be provided to facilitate movement of the device along a selected vessel, tendon, etc. Also, auxiliary means are provided as desired to handle other tasks, such as the severing of connective tissue and side branches of the vessel or other structure.

The devices of the present invention are useful in a diversity of specific medical procedures. A preferred embodiment is described with respect to the visualization and harvesting of the saphenous vein. It will be appreciated, however, that the devices and methods are equally suitable to other procedures. In one respect, the inventive method involves the placement of a light source posterior to a selected vessel and the use of light transmitted through the person's skin to visualize the location and structure of the vessel. This transillumination of the vessel is used to assist in guiding the device along the vessel, and particularly in some aspects to dissect the vessel from the surrounding tissue, address the issue of side branches, and ultimately remove the vessel. The devices and methods include retaining structures by which the vessel is positioned relative to the dissecting tip to assist in the movement of the device relative to the vessel. As a consequence of the invention, a minimally-invasive procedure is achieved which is relatively quick and causes reduced trauma as compared to prior art techniques and systems.

A preferred embodiment of the dissector device 10 of the present invention is shown in FIG. 1. The dissector 10 includes a shaft 11 having a handle 12 attached to the proximal end and a dissecting tip 13 attached to the distal end. As shown in the drawings, the shaft may be either solid or hollow, depending on the application. The tip may be either integral with or detachably connected to the shaft. The shaft and tip may comprise any material having suitable strength, resiliency and biocompatibility, and suitable materials are well known in the art.

The handle is configured to permit the required control and manipulation of the device in use. While the handle may vary with the intended use of the device, an advantageous design is shown in FIG. 1 in which the handle includes a grip portion 14 and a push pad 15. Typical use of the device 10 may involve a one-handed procedure with the hand grasping the grip portion 14. Alternatively, the push pad 15 enables a second hand to be used for greater control or to apply an increased force to move the device forward.

The shaft 11 is shown with a slight upward bend as the shaft extends forward from the handle. This bend is provided for use in the procedure of harvesting the saphenous vein, since it provides clearance for the handle from the patient's foot or ankle during extension of the device from the lower extremity of the leg. For this application, the shaft preferably includes a bend of up to about 45°, more preferably from about 10° to about 30°. Alternatively, the shaft may be straight, arcuate or otherwise shaped, including multiple bends or curves, to suit a particular use.

A dissecting tip 13 is attached to the distal end of the shaft and is configured to facilitate movement of the tip and associated shaft through the body tissue adjacent the vessel. In general, the tip 13 includes a shallow body 16. The size of the dissecting tip, particularly the length, width and thickness, is preferably adapted to the intended use of the device. In a preferred embodiment, the tip is generally concave in shape, facing upwardly in relation to the handle.

The leading, distal edge 17 of the tip is preferably contoured to enhance the ability of the tip to retain the vessel in position and to dissect the vessel from the adjoining body tissue as the device is moved forward. The leading edge may include blunt or sharp portions, or both, and typically has a tapered shape, although other designs are useful in the broadest application of the invention.

In one aspect, a light source is mounted to the device adjacent the dissecting tip. As described hereafter, the light source is provided in association with the dissecting tip in a manner which provides for transillumination of the subject vessel. The term light source is used herein to generally designate a wide variety of devices for providing light, and may include such different types of light sources as actual light-generating devices or fiber optic light sources. The light may be in any suitable spectrum, including visible and infrared (IR).

Figure 2:
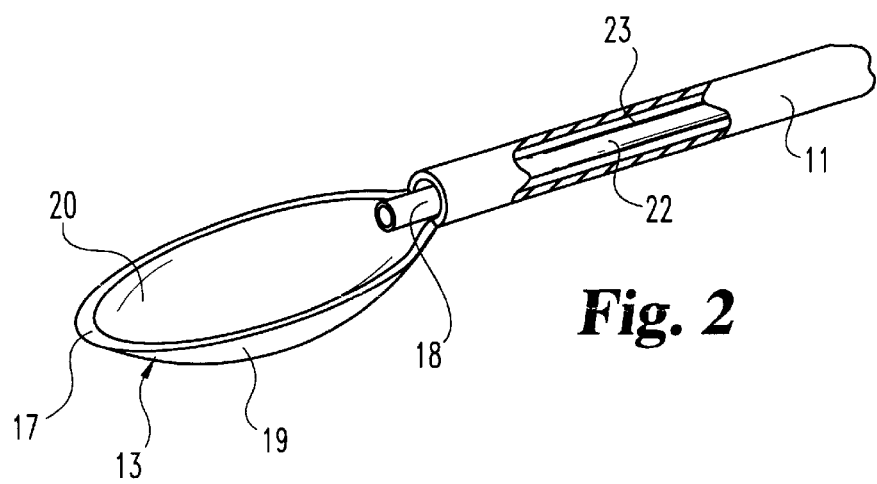
FIG. 2 is a perspective view of a preferred embodiment of a dissecting tip useful in the present invention.

In the embodiment shown in FIG. 2, the light source comprises a light 18 positioned above and displaced proximally of the distal edge of the tip. In this embodiment, the tip has a concave body 19 and a reflective upper surface 20. More particularly, the body and reflective surface are contoured to optimize the reflection of light from the light 18 in a lateral, upward direction, thereby transilluminating the vessel through the person's skin. For example, the concave reflecting surface may be such as to define a focal point and the light may then be positioned at about the focal point to cause reflected light to pass substantially parallel and laterally, i.e., transverse of the axis of the shaft and tip.

Figure 3:
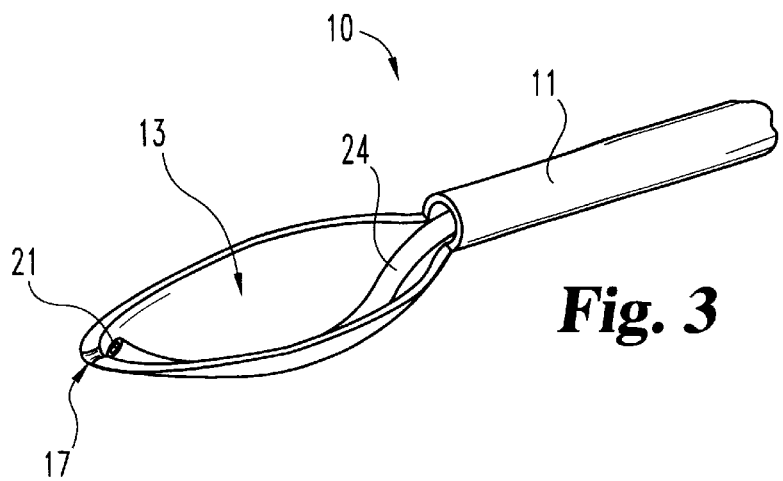
FIG. 3 is an alternate embodiment of a dissecting tip of the present invention, showing a particular design for including a light source.
Figure 4:
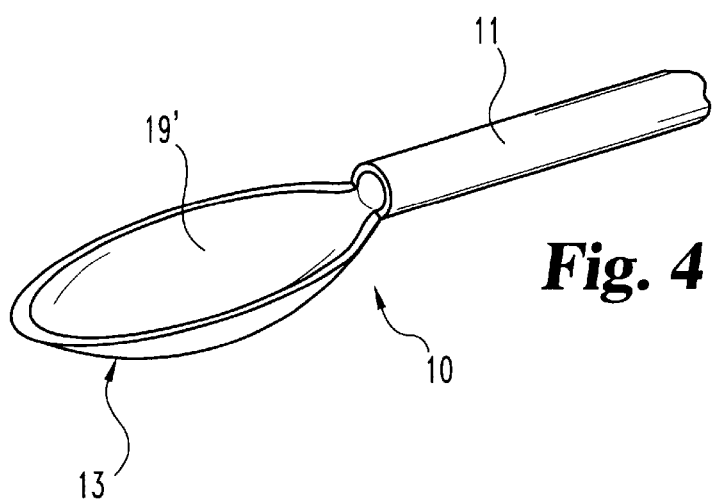
FIG. 4 is a further alternative design of the dissecting tip including a light emitting body.

Alternate embodiments are also useful for providing light in the present invention. In FIG. 3 there is shown an embodiment in which a light source 21 is located at the distal end of the dissecting tip. Similarly, the distal tip may include one or more light sources positioned at various locations along the upper surface in a regular or irregular array selected to provide the desired transillumination effect. The embodiment of FIG. 4 provides still another lighting approach in which the body 19' is itself the light source. This may be accomplished, for example, by the use of fiber optic material and suitable selection and treatment of the dissecting tip body, and particularly the upper surface of the body or the edge surrounding the upper surface.

It is a feature of the present invention that the light source is selected to provide an amount of light sufficient to transilluminate the vessel to be visible through the skin. Thus, the type, color, intensity and other parameters of the light are selected to provide the required degree of illumination. Similarly, it is advantageous, though not essential, that the light be configured and directed to optimize its utility in transillumination. For example, in a preferred embodiment the light emanating from the light source is primarily directed laterally, i.e., perpendicular to the skin surface. A light source which directs at least about 50%, more preferably at least about 80%, of the light in a lateral direction has the advantage of providing greater efficiency in the use of the light energy, and will also reduce undesirable scattering of the light and reduced visualization of the vessel.

The light sources are embodied in the dissection device in accordance with known techniques. A lighting device may be coupled through wires (not shown) extending within a conduit 22 in the lumen 23 of (FIG. 2) shaft 11, the wires connecting to an internal power source, such as batteries (not shown) located in the handle, or an external power source. Similarly, optical fibers, such as 24 (FIG. 3), may extend along and/or through the tip and shaft to a suitable light source in the handle or external of the device.

Figure 5:
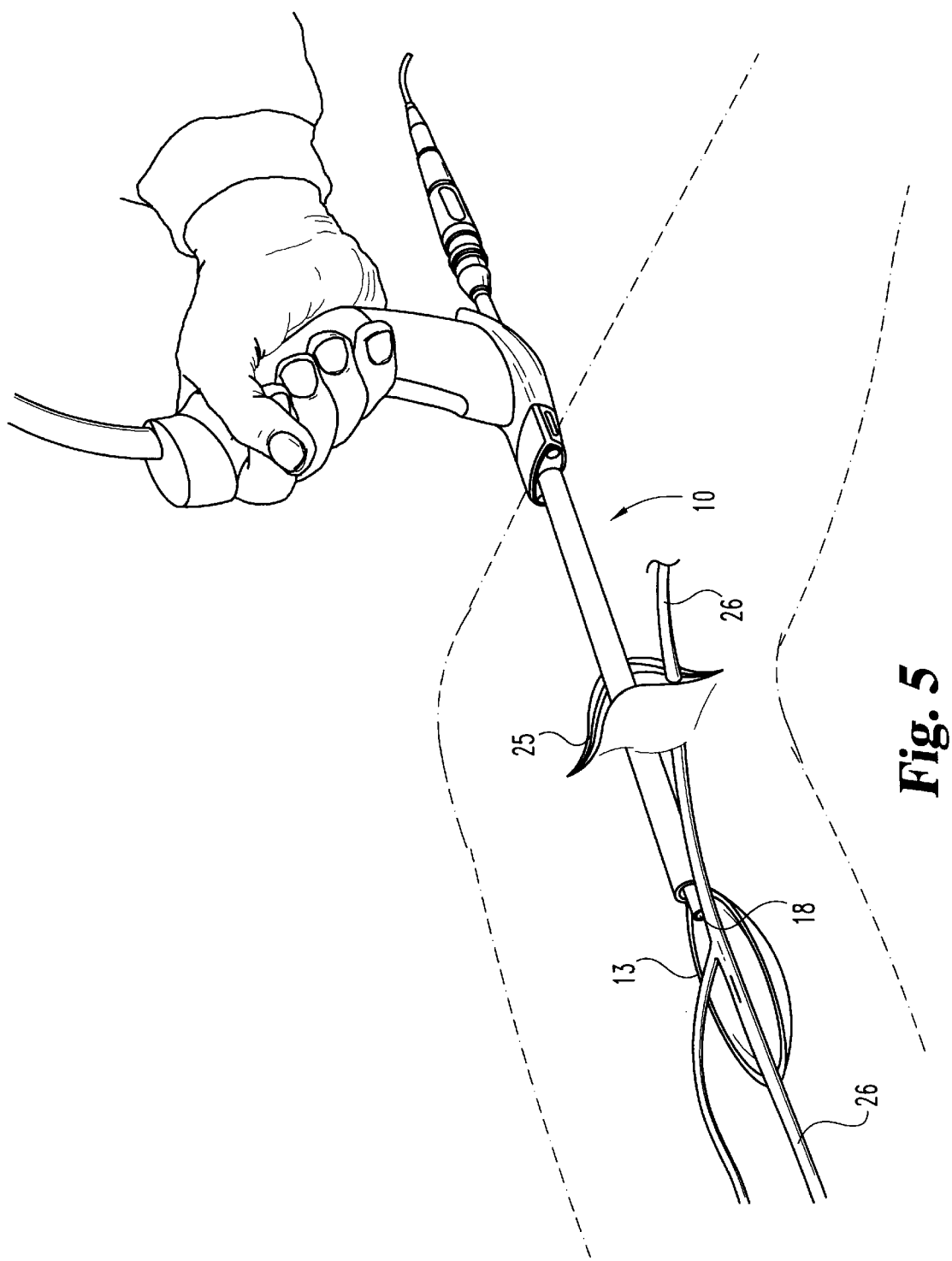
FIG. 5 is a perspective view showing the use of the present invention for transilluminating a vessel.

Utilizing the foregoing device including lighting means, a method for transilluminating a vessel or the like is readily accomplished. Referring in particular to FIG. 5, the procedure begins with making a short incision 25 adjacent the vessel 26. The proximal part of the vessel may be transected and withdrawn from the leg, as shown in FIG. 5, or simply, and frequently preferably, left intact and simply located for placement of the device. The device 10 is inserted through the incision and the distal tip 13 and light source 18 are positioned posterior of the vessel. The tip and light source are configured to direct light transversely in the direction of the vessel, which is thereby illuminated to be viewed exterior of the patient through the skin.

The device 10 is then moved forwardly into the patient along the posterior side of the vessel with the assistance of the transillumination of the vessel as a guide. The movement of the device is useful in itself in allowing the doctor to visualize the vessel as to its position and structure. In addition, the device is useful for separating the vessel from the surrounding tissue, and ultimately to enable ready removal of the vessel from the patient, if desired.

The present invention also contemplates the use of tubing inserted into the lumen of the vessel. In one aspect, the intraluminal tubing is opaque to aid in visualizing the vessel. Alternatively, the intraluminal tubing is provided with a light source which can be used in conjunction with the light provided by the dissecting tip to facilitate visualization of the vessel and/or positioning of the dissecting tip relative to the vessel. For example, the light from the interluminal tubing may be aligned with or centered within the light of the dissecting tip, or aligned between a plurality of lights of the tip, to assure desired positioning. The lights can be provided to be the same or different in color, intensity, etc. to provide contrast between the dissecting tip and the interluminal tubing, further enhancing the manipulation of one relative the other.

Figure 6:
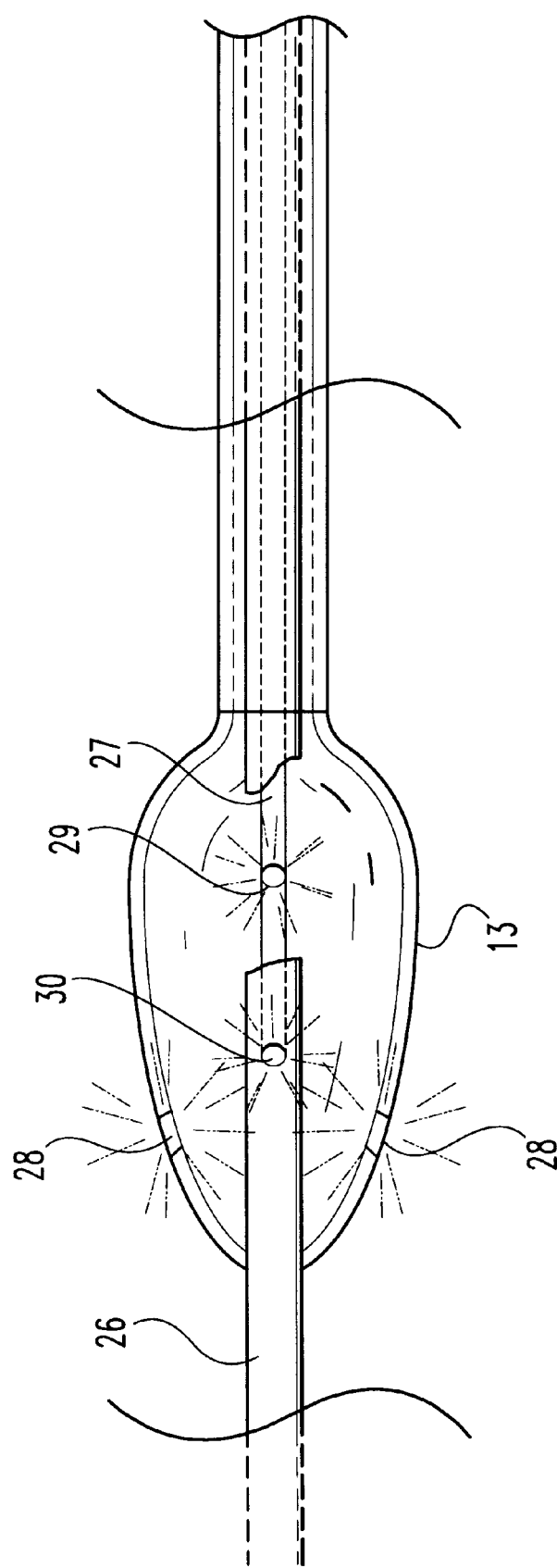
FIG. 6 is a top, plan view showing the use of the transillumination feature of the present invention in conjunction with intraluminal tubing placed within the subject vessel.

Referring in particular to FIG. 6, there is shown an example of the use of interluminal tubing and transillumination in accordance with the present invention. Opaque tubing 27 is shown received with vessel 26. An illuminating tip 13 includes a pair of optical fiber light sources 28 near the distal end. As the tip is passed posterior of the vessel, the opaqueness of the tubing 27 enhances the illumination of the vessel by increasing the contrast of the vessel structure in the light field. In addition, the tubing is shown with a pair of optical fiber light sources 29 and 30. As the tip 13 is moved forward, the opaque tubing and vessel, and particularly the light sources 29 and 30, are maintained in position between the lights 28 to assist in guiding the tip.

Dissection of a vessel or other elongated structure using transillumination is accomplished in the following manner. As described with respect to transillumination, the first step is to make an incision in the body adjacent the target structure, e.g., vessel. A dissecting device is then inserted into the person through the incision, with the dissecting device including a dissecting tip and a light source mounted adjacent to the dissecting tip and directing light laterally. The dissecting tip and light source are then positioned posterior of the vessel with light directed laterally outward in the direction of the vessel. The dissecting device is advanced along the vessel, while visualizing the vessel through the person's skin by means of the light directed by the light source past the vessel and through the person's skin. As the device progresses, the vessel is dissected from the surrounding tissue.

The foregoing method is performed with any of the preceding transillumination devices. As described subsequently, this procedure is similarly accomplished with the dissecting devices described hereafter which include retaining structures for retaining the dissecting tip adjacent the vessel as the device is moved along the vessel. With suitable retaining structures, the need for transillumination may be obviated, and the following description therefore contemplates a device and its use with or without transillumination.

The procedures of the present invention may further include additional steps leading to the transection and ultimate harvesting of the vessel. In this regard, in conjunction with advancing the dissection device along the vessel, the vessel is transected at proximal and distal locations to obtain the desired length of vessel for harvesting. The transected vessel dissected from the surrounding tissue is removed from the body. In accordance with such methods, side branches of the vessel are transected, or alternatively ligated and transected, as they are encountered. Cauterization of one or more side branches may also be employed as is understood in the art.

In one preferred application of the device and method, the saphenous vein is harvested from the patient. The procedure is particularly advantageous in that there is reduced trauma to the patient since only short incisions, typically in the range of 2 cm, are required. In some procedures, such as for the saphenous vein, the procedure may employ two or more incisions to allow for reintroduction of the dissection device at different points along the length of the vessel. This allows for the dissection device to be shorter and therefore more manageable, while still being useful to retrieve the full length of the vessel.

It also appears that in certain instances, such as for the saphenous vein, any side branches which may be encountered tend not to extend directly inwardly or outwardly relative to the skin. Thus, the dissection device can be readily extended into the patient and the side branches are well transilluminated by the light source when used. As is discussed more fully hereafter, the side branches can be separated from the main vessel by means associated with the dissection device, and the vessel thereafter removed.

The shaft, as previously noted, may be either solid or hollow in construction. The use of a hollow shaft permits the extension of various devices through the shaft. Such devices would include one or more ligation, suction, irrigation or other devices known in the endoscopic art. The devices may be used, for example, to inject fluids, medicaments, gases or the like into the site. As more particularly described hereafter, clipping and ligating instruments may similarly be introduced in this fashion to complement the operation of the dissecting tip.

The present invention also provides various unique design features for the dissection device, and particularly the dissecting tip. In particular, the dissecting tip preferably includes one or more structures to retain the tip in position adjacent the selected vessel as the tip is advanced relative to the vessel. These design features enhance the utility of the device in particular methods, including for example the harvesting of the saphenous vein. These features are advantageous both with and without the presence of the lighting source previously described.

The dissecting tip preferably includes a generally tapered design with a reduced profile at the tip to assist in insertion of the tip into the tissue surrounding the vessel or other structure. One form of retaining structure comprises recesses, projections or other shapes adjacent to the distal end of the tip to facilitate moving the tip along the proper course to track closely with the position of the vessel. As the distal end progresses through the tissue, it is important that it does not divert significantly from the location of the vessel. At the same time, the distal end provides the initial dissection of tissue.

A second form of retaining structure comprises recesses, projections or other shapes displaced from the distal end of the dissecting tip to complete the dissection of tissue from around the vessel and to transect side branches as necessary. It is a feature of certain of these retaining structures that the vessel can be received within an essentially all-encompassing structure, thereby assisting in maintaining the tip in position along the vessel.

Figure 7:
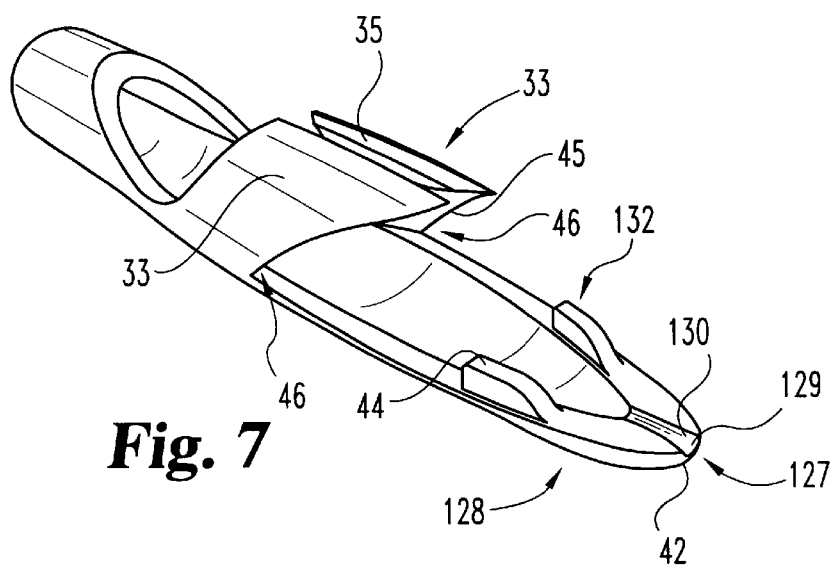
FIG. 7 is a perspective view of an embodiment of the dissecting tip showing several retaining structures.
Figure 8:
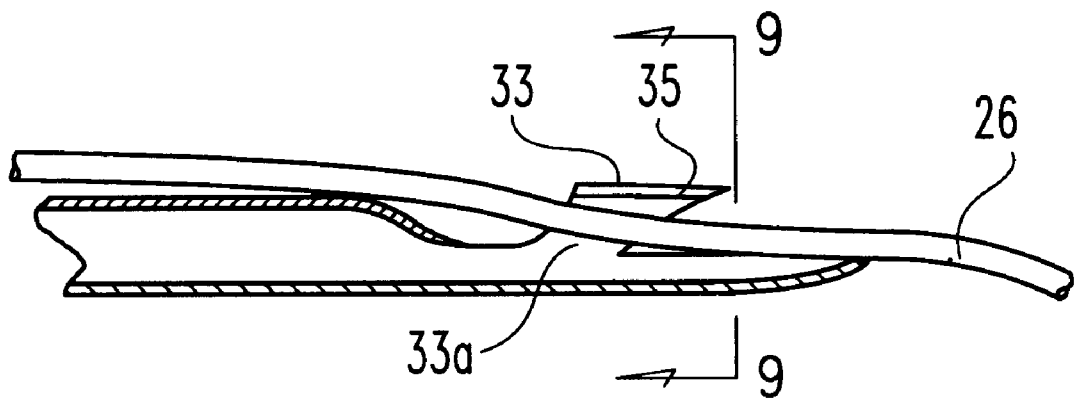
FIG. 8 is a side, cross-sectional view of the embodiment of FIG. 6 with a vessel received within the retaining structures.
Figure 9:
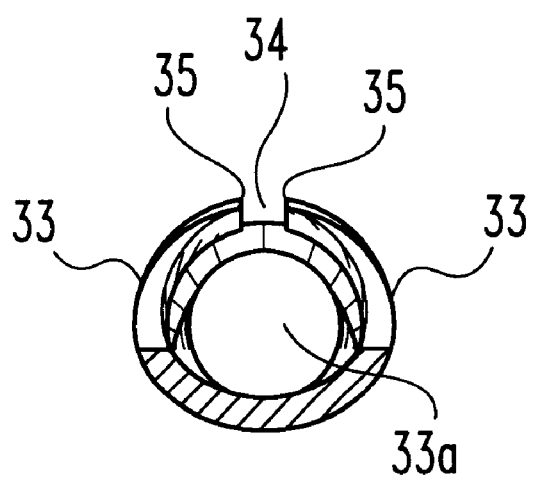
FIG. 9 is a front, cross-sectional view of a version of the dissecting tip which includes mutually facing arms for retaining a vessel.
Figure 10:
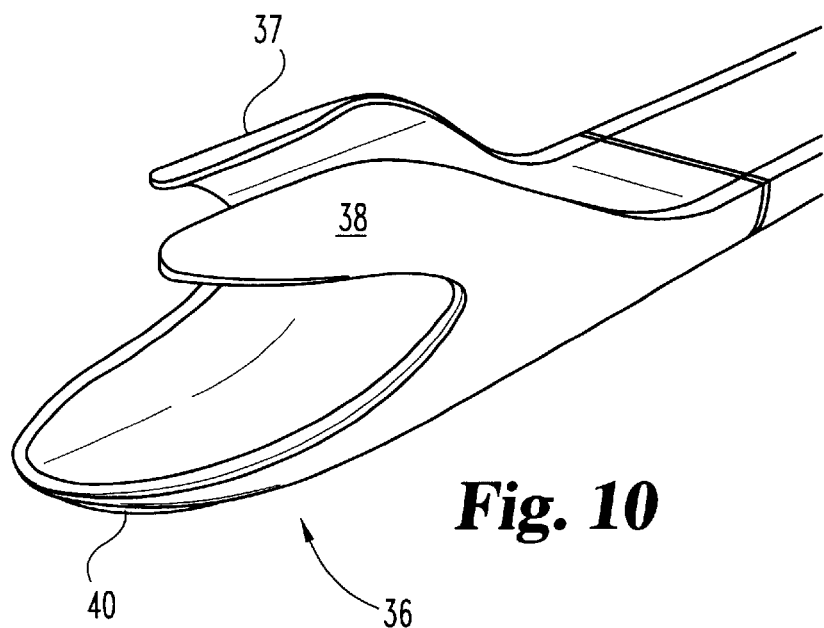
FIGS. 10 and 11 are perspective views of an alternate embodiment of the dissecting tip showing overlapping retaining arms.
Figure 11:
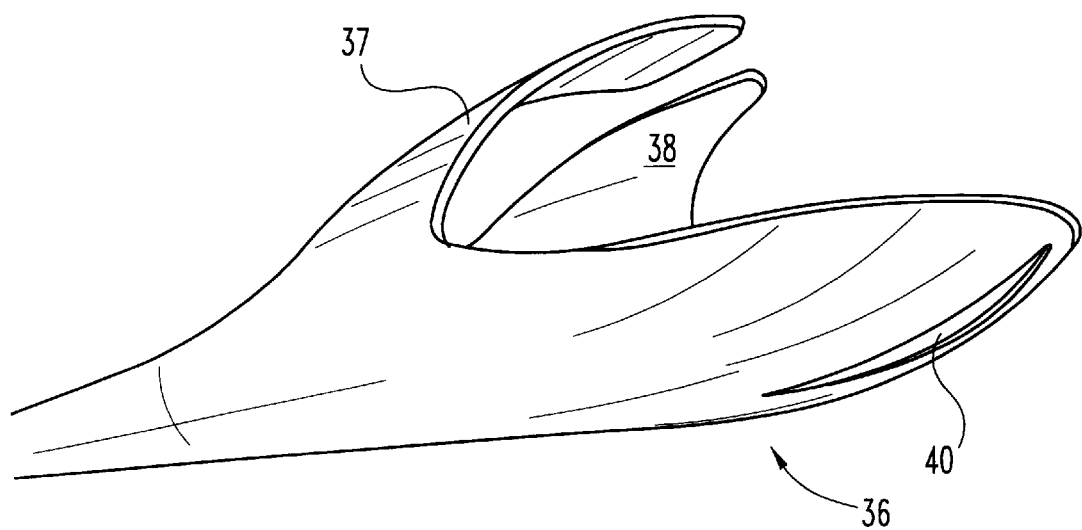
Figure 12:
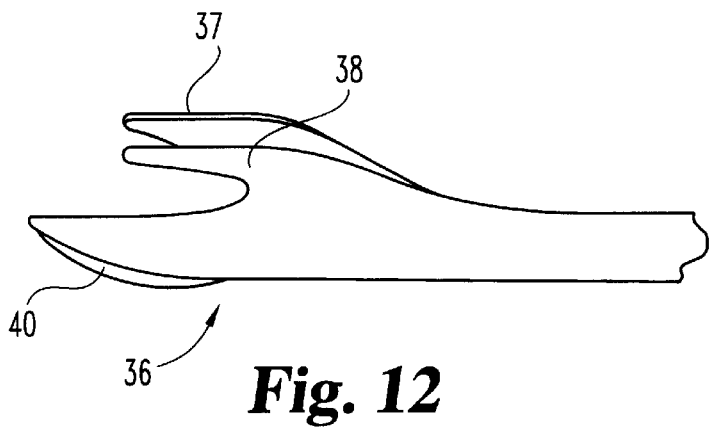
FIG. 12 is a side, elevational view of the embodiment of FIG. 10.
Figure 13:
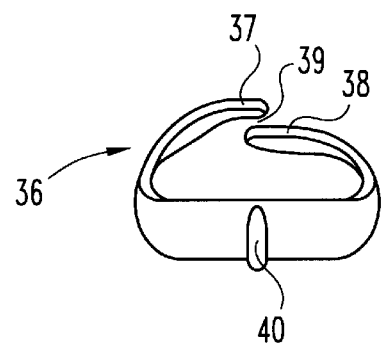
FIG. 13 is a front, elevational view of the embodiment of FIG. 10.
Figure 14:
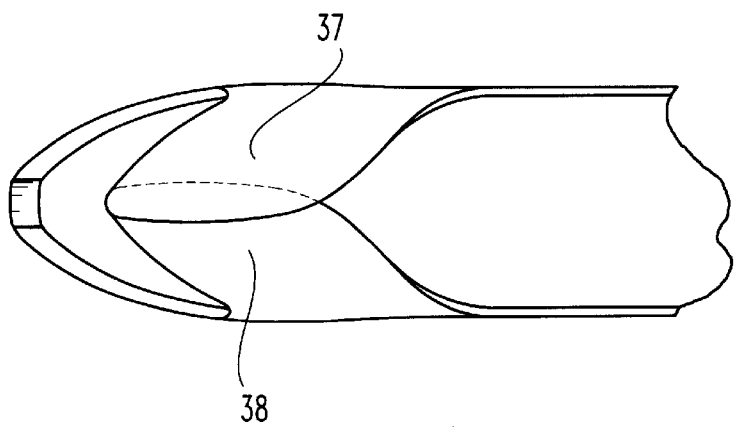
FIG. 14 is a top, plan view of the embodiment of FIG. 10.

An alternate embodiment of the dissecting tip is shown in FIGS. 7–9, in which the tip includes a trough 127 formed at the distal end of the tip 128. The trough comprises a central area which is displaced downwardly of the adjacent portions of the tip, thereby defining a central platform 129 and a pair of mutually facing side walls 130. The vessel 26 (FIG. 8) is received therein against the platform and between the side walls 130. Similarly, the dissecting tip may include a pair of tabs 132 which extend upwardly at the distal end of the tip for reception of a vessel therebetween. It will be appreciated that these two types of retaining structures are comparable in retaining the distal end of the dissecting device in position relative to the vessel, and may be used separately or together. Further variations of these design features which hold the vein in relative lateral position relative to the distal end of the dissecting tip are equally useful.

A further retaining structure is provided by a pair of arms 33 which extend upwardly from the tip at a location displaced from the distal end of said tip, and which define a confinement space 33a for reception of the vessel. The upstanding arms preferably include at most a relatively small gap 34 between the mutually-facing ends 35 of the arms to enhance the ability of the arms to retain the vessel in the area below the arms. The small gap 34 is sized sufficient to allow the vessel to be received therebetween, but in a relatively close fit to maximize the ability of the arms to retain the vessel in place. One approach is to size the gap as approximately the diameter of the target vessel. However, the gap may actually be sized substantially smaller and still operate to receive the vessel therethrough, for example by making the gap about the size of the vessel when it is collapsed, e.g., about two wall thicknesses.

In alternate designs, the arms 33 have other configurations. Shown in FIGS. 10–14 is a design in which the arms slightly overlap laterally, one over the other, and are spaced apart from one another a distance sufficient to receive a vessel therebetween. For example, the device 36 includes one arm 37 which is positioned above and overlaps the second arm 38. A small gap 39 (FIG. 13) remains between the overlapping arms to permit the vessel, tendon or the like to be moved into position between and below the arms. Also shown in this embodiment is a keel 40 extending along the underside of the tip to facilitate control of the device as it is moved forward.

Figure 15:
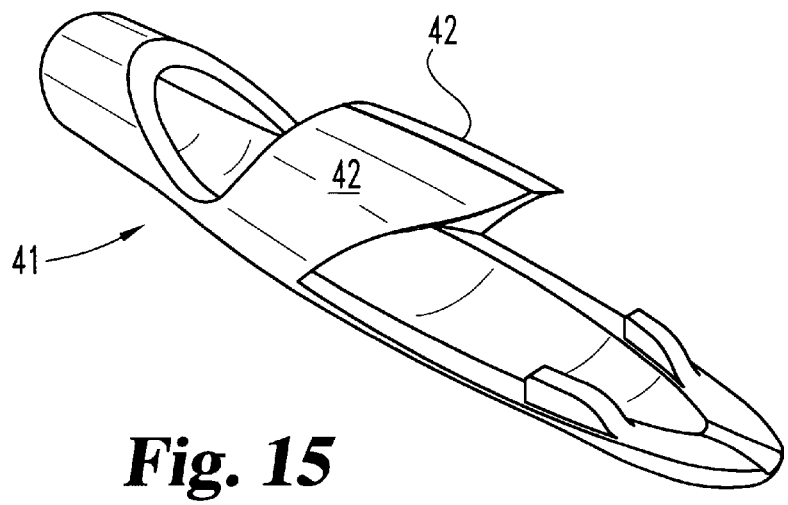
FIG. 15 is a perspective view of an alternate embodiment of the dissecting tip showing abutting retaining arms.
Figure 16:
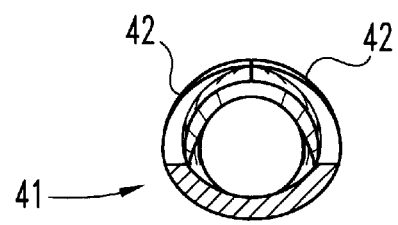
FIG. 16 is a front, cross-sectional view of the embodiment of FIG. 15, looking backward from in front of the retaining arms.

In FIGS. 15–16 is shown an embodiment 41 including a pair of arms 42 which terminate in ends which are mutually-facing and which abut one another. These arms are preferably sufficiently flexible and spring loaded to permit displacement of the ends of the arms away from each other a sufficient distance to permit a vessel or the like to be received therebetween. Alternatively, a closed connection of the arms, or an integral wall, can be used, in which case the vessel is transected and then placed through the space underlying the arms.

These retaining arms of various configuration all serve the purpose of confining the vessel within the dissecting tip as the tip progresses through the surrounding tissue. In general, the retaining arms provide a means for surrounding the vessel at a location displaced from the distal end of the tip. At the same time, means are also provided to enable the vessel to be moved from outside of the enclosure defined by the arms to inside the enclosure. As indicated, such means can be provided by using arms that have a narrow gap therebetween or that abut but are separable.

Alternative designs are also contemplated which otherwise provide for placing the vessel within the enclosing arms but protecting against the vessel coming back out from inside the arms as the tip is being advanced through the tissue. For example, a spring-biased lever may be incorporated into one of the arms which permits only movement in the inward direction. Such a lever would permit the vessel to be moved into the arms, but would prevent movement in the opposite direction. Such a lever can be readily provided by means of a "living hinge" integrally connecting the lever portion with the rest of the supporting arm.

Figure 17:
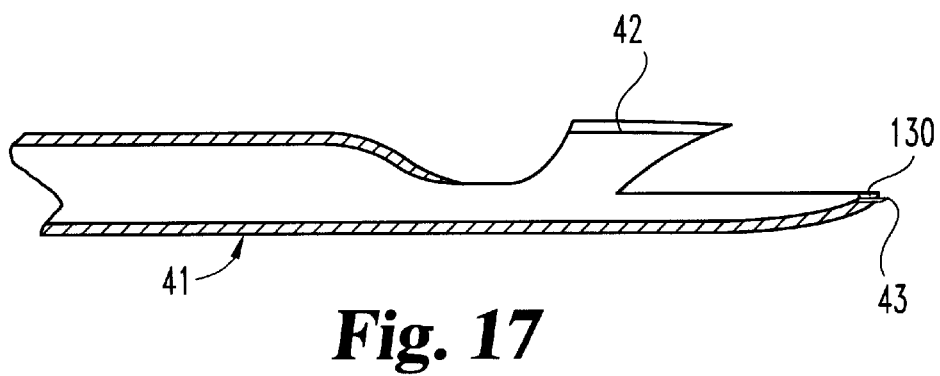
FIG. 17 is a side, cross-sectional view of the embodiment of FIG. 16.

The device further preferably includes surfaces which facilitate the dissection of the vessel from the surrounding tissue, as well as transection of side branches of the vessel. Referring to FIG. 7, the dissecting tip 28 includes a leading edge 42 which initially engages the tissue surrounding the vessel as the device 10 is moved forward. As desired for a given application, this leading edge may be provided with either a dull or sharp edge for dissecting the vessel from the surrounding tissue. Similarly, the leading edge of the central trough, when included, may also be provided with either a dull or sharp edge to suit the use of the device. The leading edge may optionally include at these locations attached cutting members, such as metal cutting blades, e.g., blades 43 (FIG. 17).

The upstanding tabs 32 have upper edges 44 which may also be either dull or sharp. In one design, the edges 44 are sharp and will have the effect of cutting through the surrounding tissue. Such sharp edges may also impact side branches of the vessel and will have utility in transecting such side branches as they are encountered. Thus, the tabs 32 can be employed for helping to retain the device in position relative to the vessel and/or to transect side branches of the vessel.

In the alternative, the tabs 32 may be provided with dull upper edges. This design maintains the use of the tabs for retaining the device adjacent the vessel, and can also be used in conjunction with subsequent cutting edges on the upstanding arms as hereafter described.

The upwardly extending arms 33 have particular use in both retaining the device adjacent the vessel and potentially in dissecting the vessel from the surrounding tissue and in transecting side branches. In addition to acting as retainers or guides, the arms in combination with the body of the dissecting tip provide a full or substantially full enclosure 34 around the vessel as the tip is advanced. The front edges 45 of the arms include portions which encounter surrounding tissue not addressed by the preceding portions of the dissecting tip. Therefore, in one aspect the front edges are provided with either dull or sharp edges, as desired, to further dissect the vessel from the adjacent tissue. Selection of dull or sharp edges is determined based on other design aspects of the dissecting tip and/or the intended use of the device.

The upwardly extending arms 33 also have particular utility in transecting side branches of the vessel. In a preferred embodiment, the front edges of the arms define notches 46 into which side branches are received as the device is moved forward. The presence of the upstanding tabs 132 will operate in conjunction with the arms by moving the side branches into position for reception within the notches. Thus, the tabs may be provided with either sharp or dull upper edges which will cooperate with the following arms, and particularly the notches 46, to transect side branches. For example, dull upper edges of the upstanding tabs will be useful in directing side branches upwardly into position against the front edges of the arms 33, and particularly into notches 46 when provided.

The dissecting tip may include cutting blades or equivalent structures at any of the positions indicated to be useful for dissecting the tissue or transecting side branches. In addition to cutting blades 43 at the leading edge of the trough 27, such blades or equivalent cutting structures are suitably incorporated at a variety of other locations including the lead and upper edges of the tabs 132, the front edges of the arms 33, and/or the notches 46.

In a further alternate design, the gap between the arms can be configured in various other ways to enhance the use of the dissecting tip. As shown in FIGS. 18–21, for example, the arms can be designed to provide an S-shaped gap which further resists accidental removal of the vessel from between the arms. A further feature of this design is that it positions the exiting of the vessel in the proximal direction at a location adjacent the bottom of the tip, rather than near the top. This can be preferable in certain applications of the device in terms of aligning and progressing the tip through the tissue.

Referring in particular to FIGS. 18–21, there is shown a dissecting tip 47 having an S-shaped gap 48. As in the previous embodiments, the body of the tip defines a central opening 49 in which the vessel is received. In particular, the vessel is received over the distal end 50 of the tip and the rounded forward end, and thereafter extends through the central opening and exits downwardly through the opening 51. In this embodiment, the S-shaped gap 48 is defined by a first portion 52 and a second portion 53. The second portion 53 includes a hooked end 54 which further serves to entrap the vessel within the gap and prevent its escape during manipulation of the device.

The dissecting tip may also be equipped for cauterization as the tip is extended through the tissue and transects the side branches of the vessel. The design and use of cauterizing implementation is well known in the art, and the present invention may employ the range of such devices. RF electricity has been used for decades to cauterize and coagulate tissue in surgical procedures. Devices used to apply RF energy to tissue fall generally into two categories: monopolar and bipolar. Bipolar electrosurgical instruments incorporate both active and return electrodes into the surgical instrument, substantially restricting the flow of electric current to tissue that is placed between the electrodes. In monopolar electrosurgical instruments, on the other hand, the return electrode is placed outside the patient's body, on the patient's skin. Thus, in a monopolar electrosurgical instrument, current flows from the active or treatment electrode through the patient's body to the return electrode. Both monopolar and bipolar electrosurgical instruments rely at least in part on resistance heating to cauterize and/or cut tissue.

Figure 22:
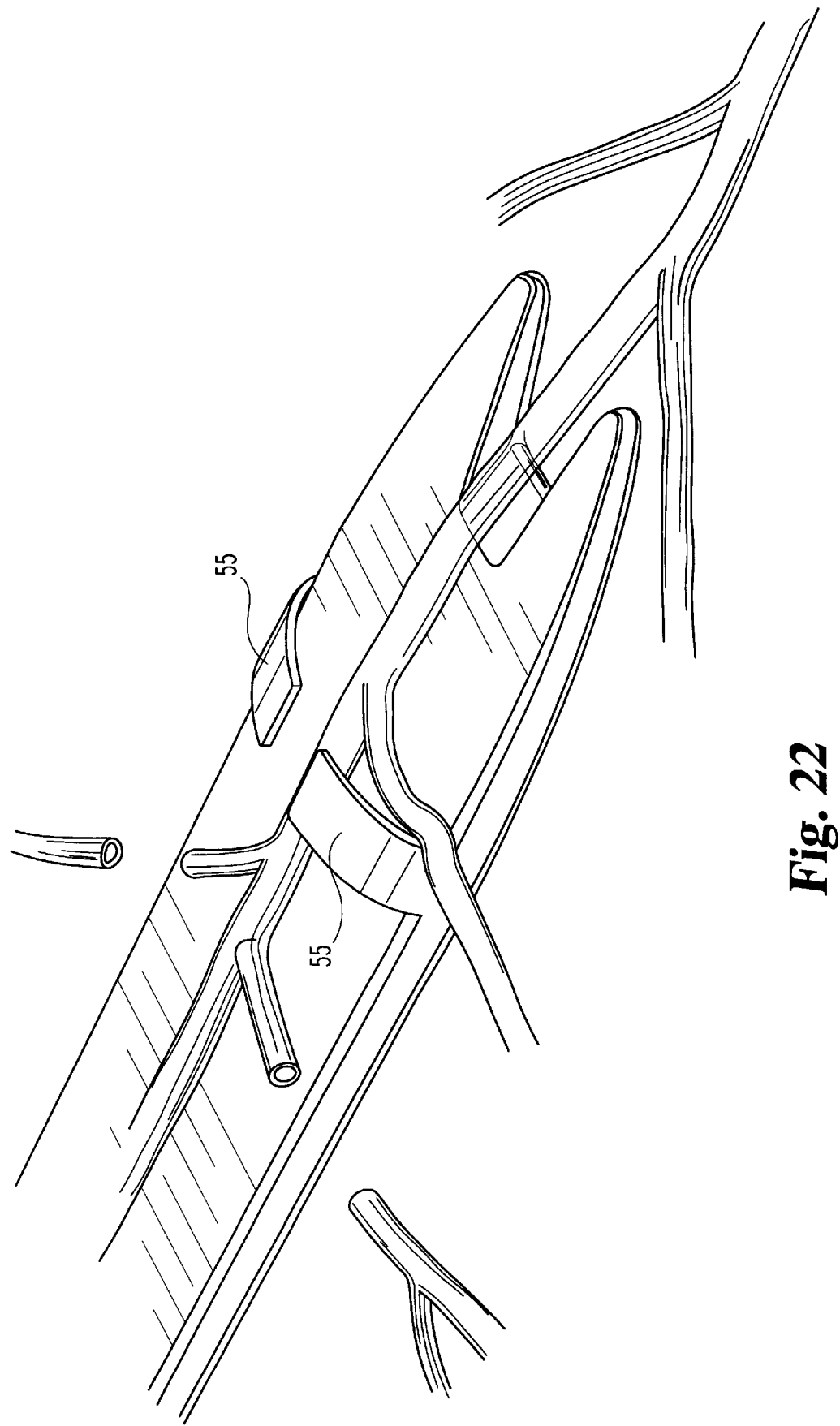
FIG. 22 is a perspective view of an embodiment of a dissection tip including monopolar cauterizing arms.
Figure 23:
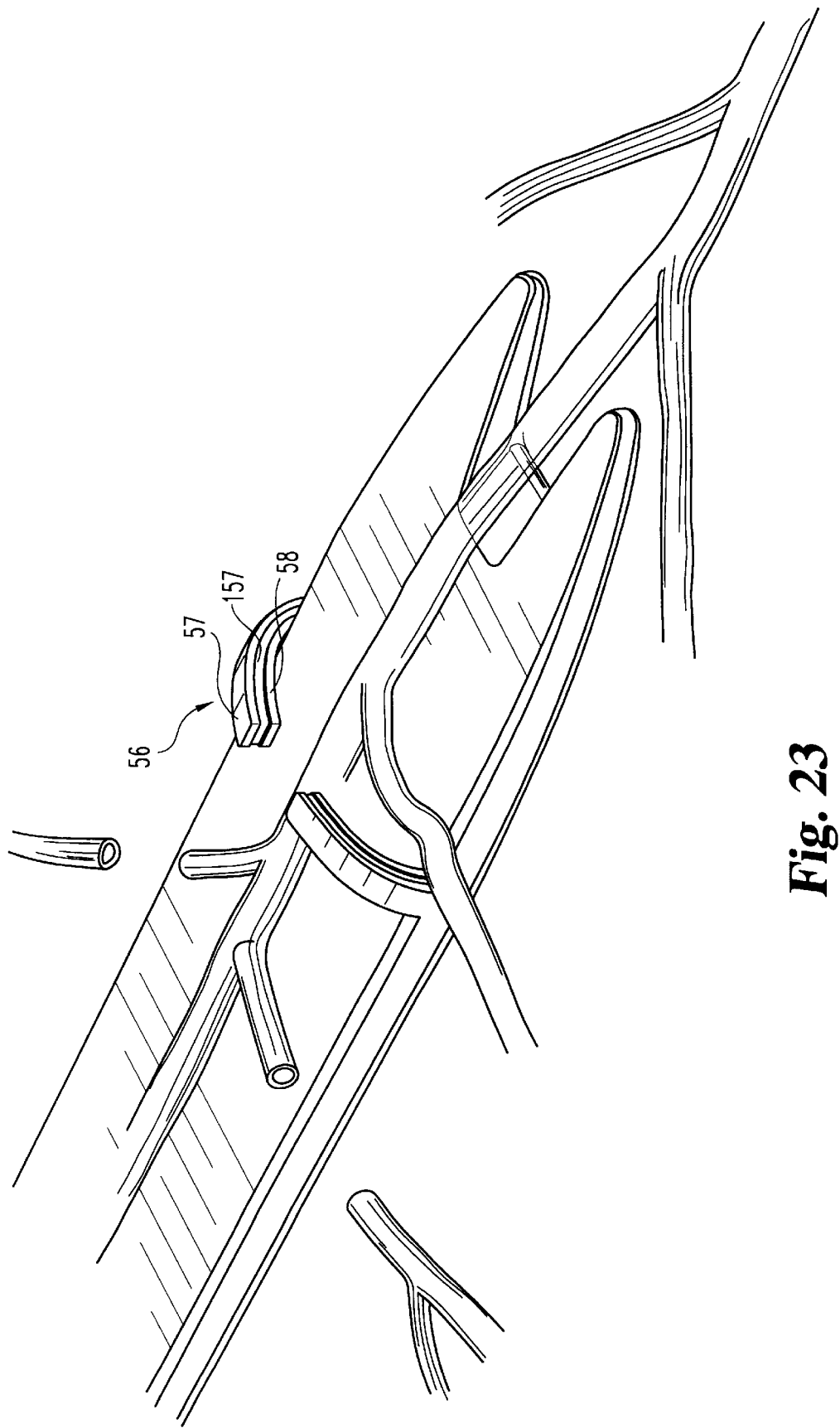
FIG. 23 is a perspective view of an embodiment of a dissection tip including bipolar cauterizing arms.
Figure 24:
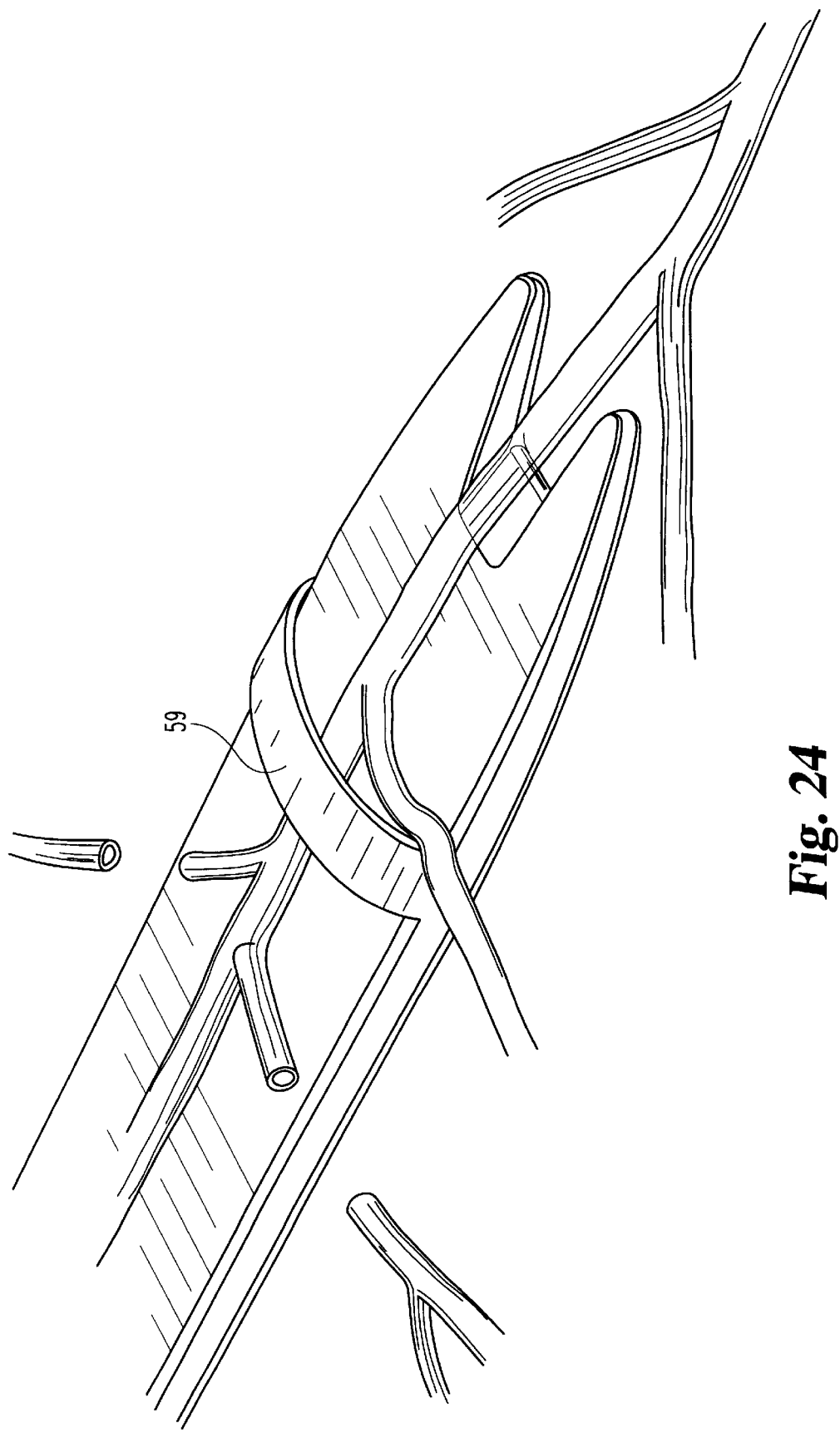
FIG. 24 is a perspective view of an embodiment of a dissection tip including a monopolar cauterizing arch.

The cauterization feature may be employed at a variety of locations of the dissecting tip in accordance with the design requirements for such devices. For example, as shown diagramatically in FIG. 22, the upstanding arms 55 may comprise monopolar wires, with the arms transecting and cauterizing the side branches as the tip is moved forward. Alternatively, the embodiment of FIG. 23 includes arms 56 comprising a pair of parallel segments 57 and 58 which incorporate bipolar wires separated by an insulating layer 157 and are used to cauterize the side branches as they are cut. A dissecting tip with a continuous arch 59, as opposed to separate arms, is shown in FIG. 24, in which the arch includes a monopolar wire used for cauterization. The full range of cautery designs, such as bipolar and monopolar RF electrodes and other energy sources, may be readily incorporated as a part of the dissecting tip of the present invention.

Figure 18:
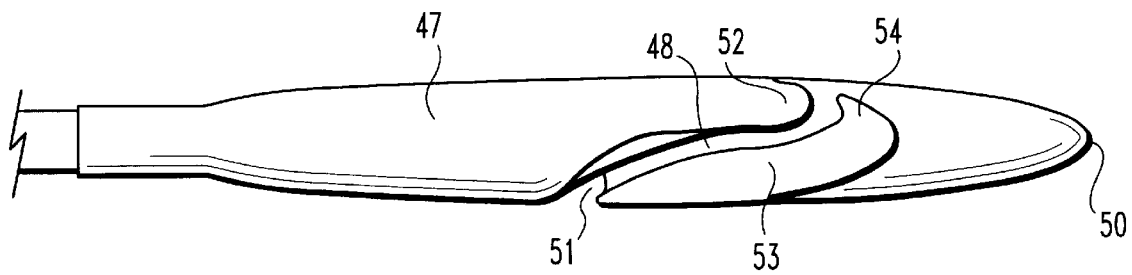
FIG. 18 is a top, plan view of an embodiment of the dissecting tip including an angled, S-shaped slot between the arms.
Figure 19:
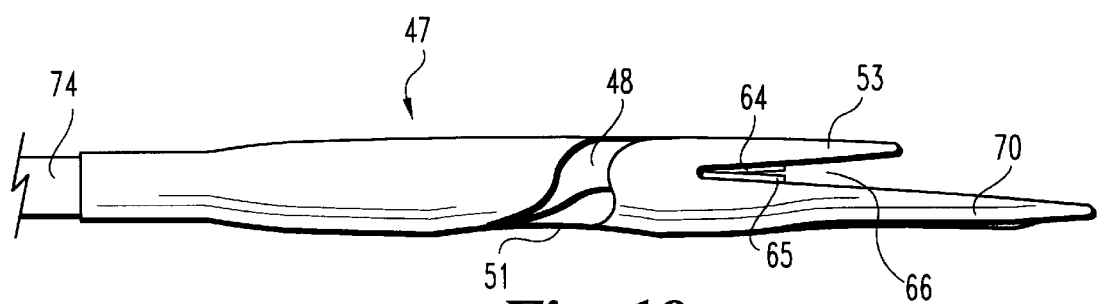
FIG. 19 is a side, elevational view of the dissecting tip of FIG. 18.
Figure 20:
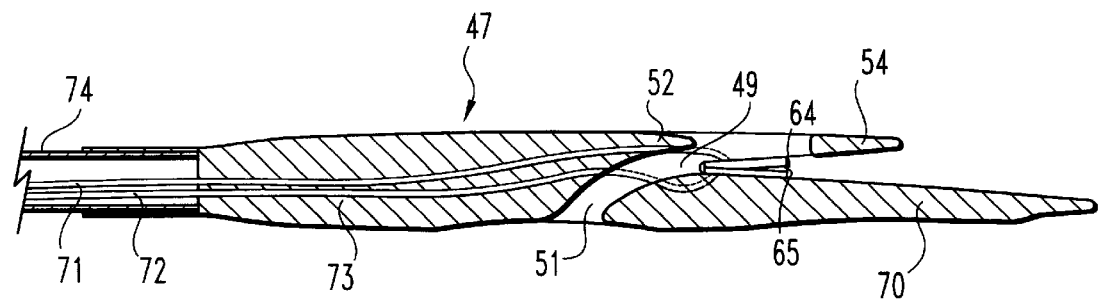
FIG. 20 is a side, cross-sectional view of the dissecting tip of FIG. 18.
Figure 21:
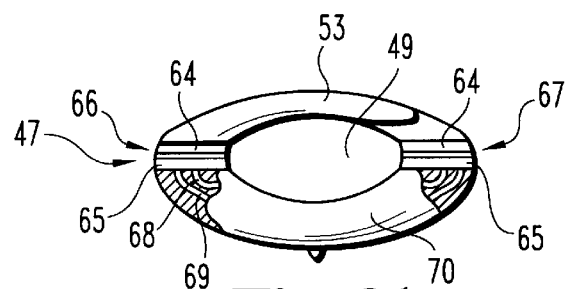
FIG. 21 is a front, elevational view of the embodiment of FIG. 18.

Referring to a further particular design for a cautery instrumentation, there is shown in FIGS. 18–20 a design including two pairs of bipolar cautery elements 64 and 65. The cautery elements are positioned within the slots 66 and 67 on opposed sides of the dissecting tip. 47. Wires 68 and 69 extend through the lower tip portion 70 to interconnect the elements in slot 66 with the elements in slot 67. Further, wires 71 and 72 connect with the cautery elements 64, 65 in slot 67 and extend through the dissecting tip body 73 and interior of shaft 74 to connect the cautery elements with an external power source (not shown). Tissue or side branches received within the slots 66 and 67 are cauterized by the application of power to the cautery elements 64 and 65 in accordance with the known operation of such cautery devices. In addition, while various designs of the cautery elements may be employed, an example of a particular cautery design useful with the present invention is disclosed in pending application Ser. No. 09/241,593, entitled RF Bipolar Mcsentery Takedown Device Including Improved Bipolar Endofactor, filed by Scott D. Wampler et al. on Feb. 2, 1999, and hereby incorporated by reference.

Figure 25:
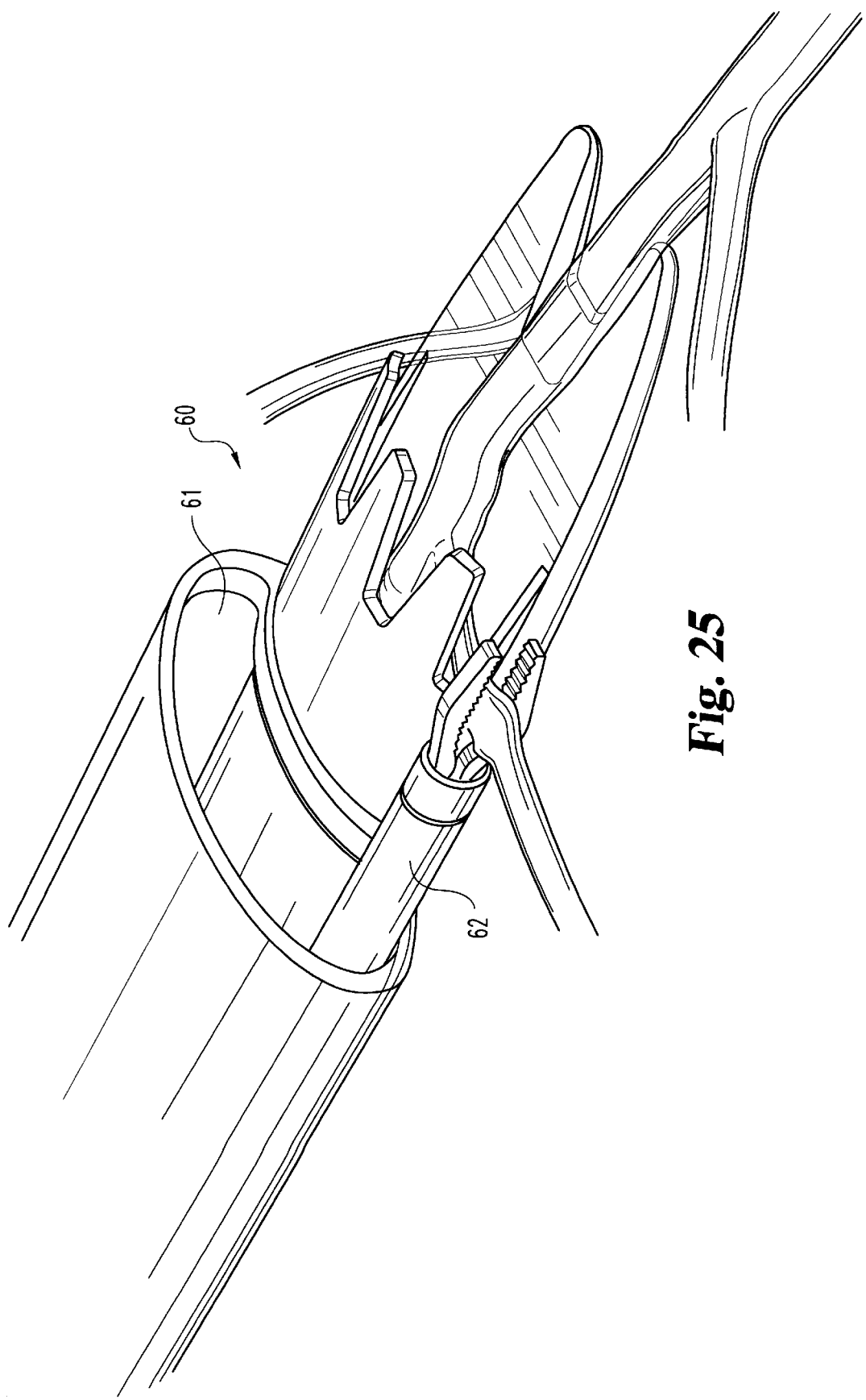
FIG. 25 is a perspective view of an embodiment of a dissection tip including an arcuate shaped lumen in the shaft.
Figure 26:
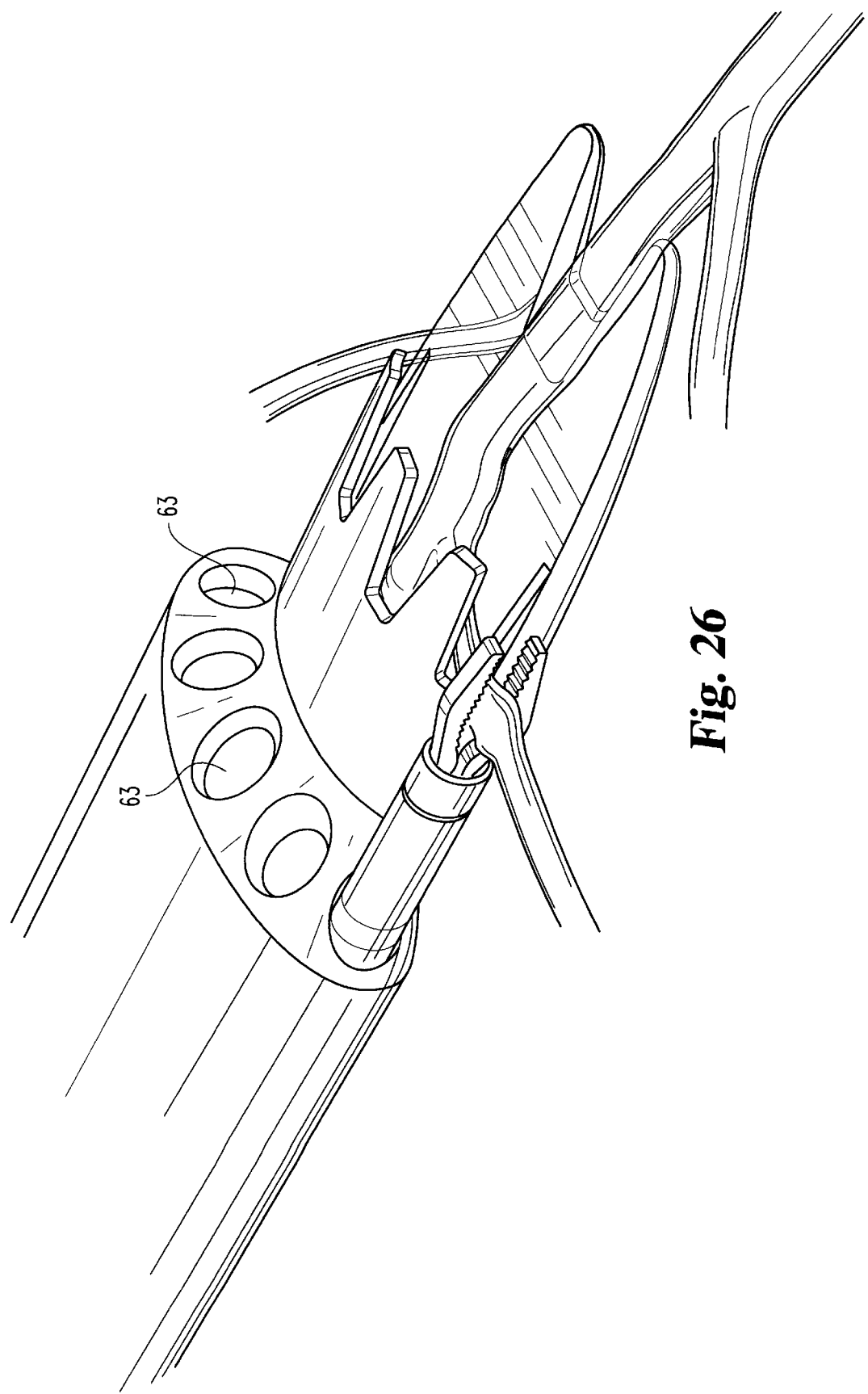
FIG. 26 is a perspective view of an embodiment of a dissection tip including a plurality of lumens in the shaft.
Figure 27:
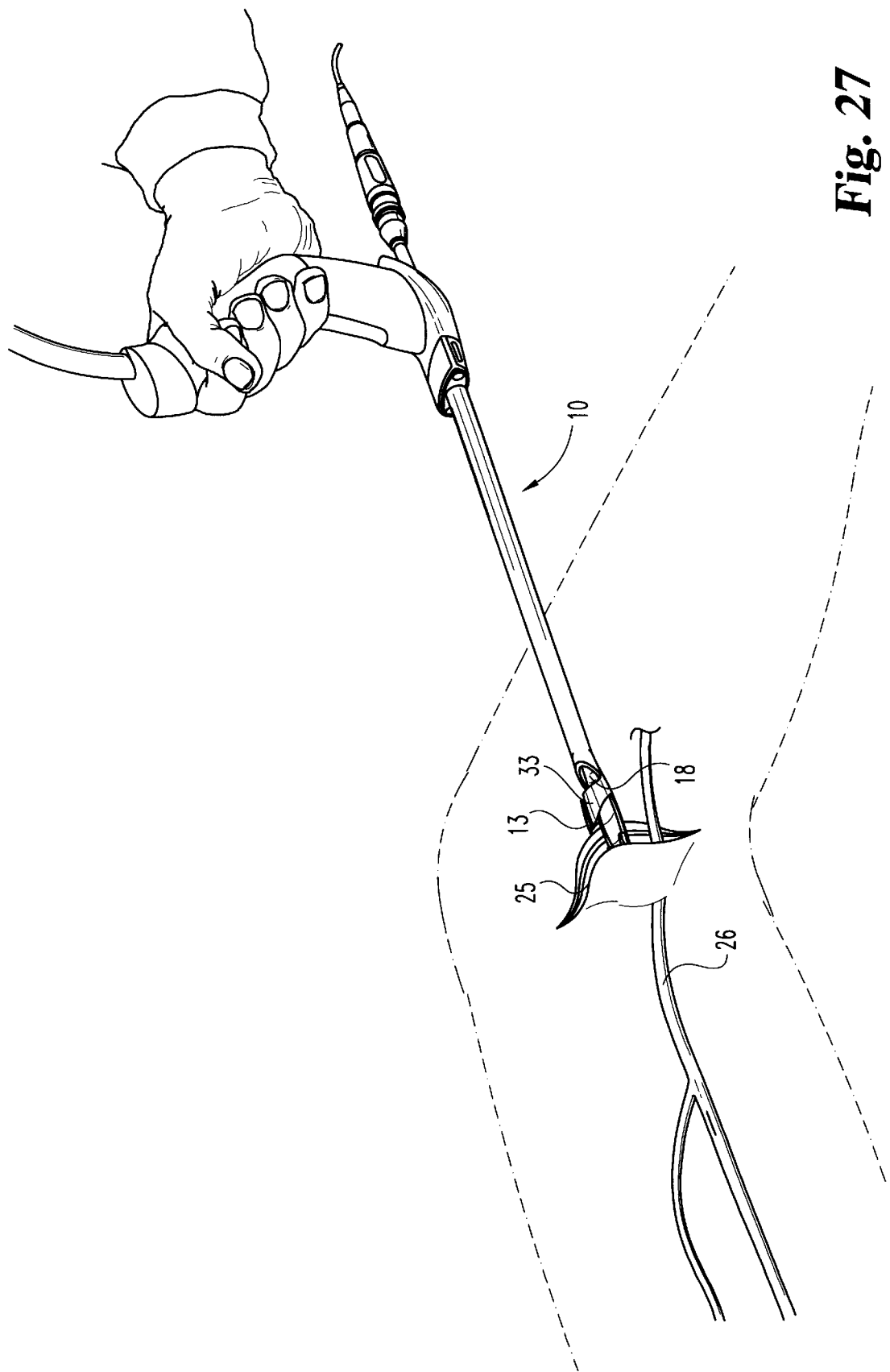
FIG. 27 is a perspective view showing the initial insertion of the distal end of a dissecting device in a method of the present invention.
Figure 28:
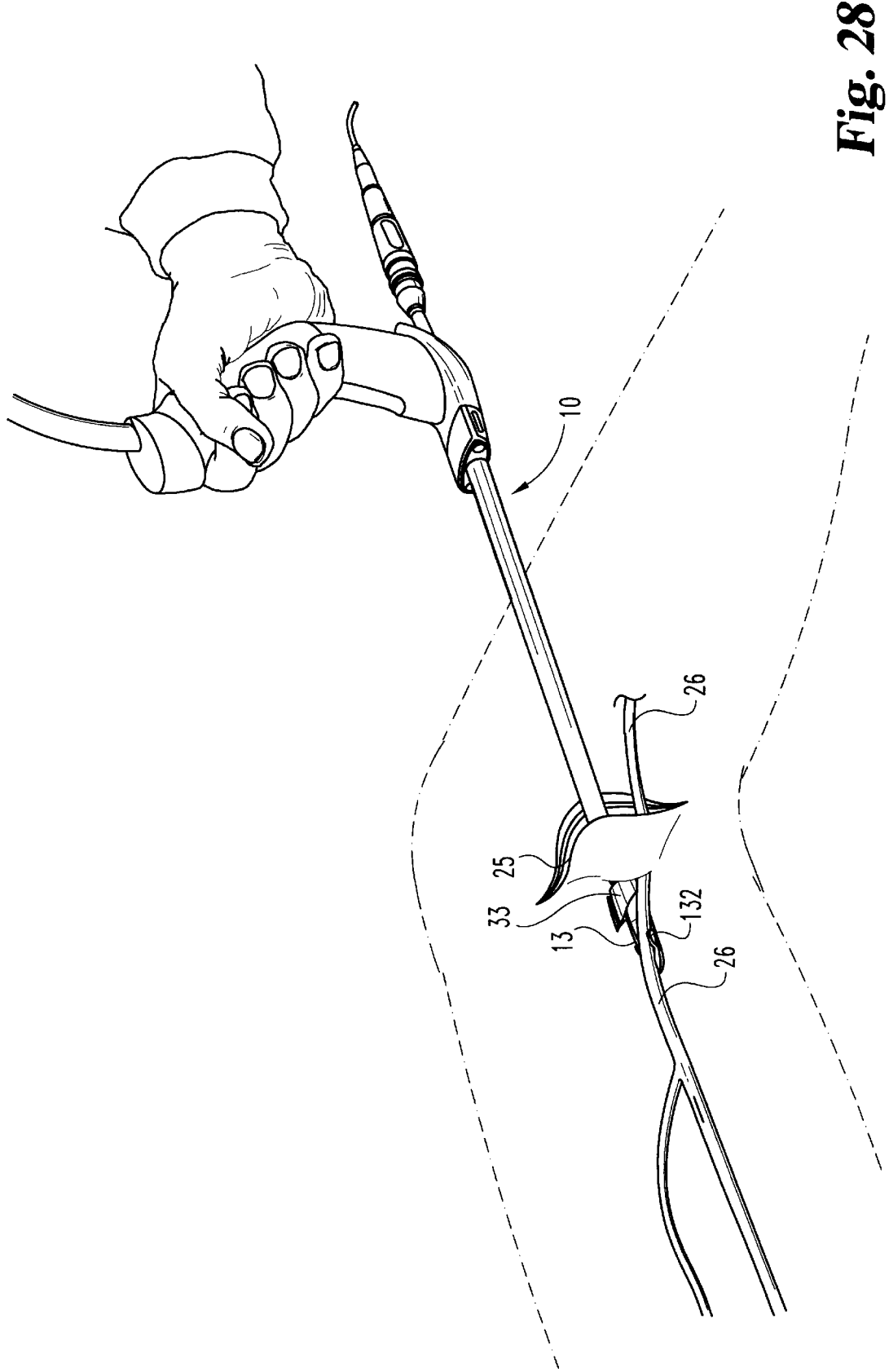
FIG. 28 is a perspective view showing the insertion of the dissecting device prior to encountering a side branch.
Figure 29:
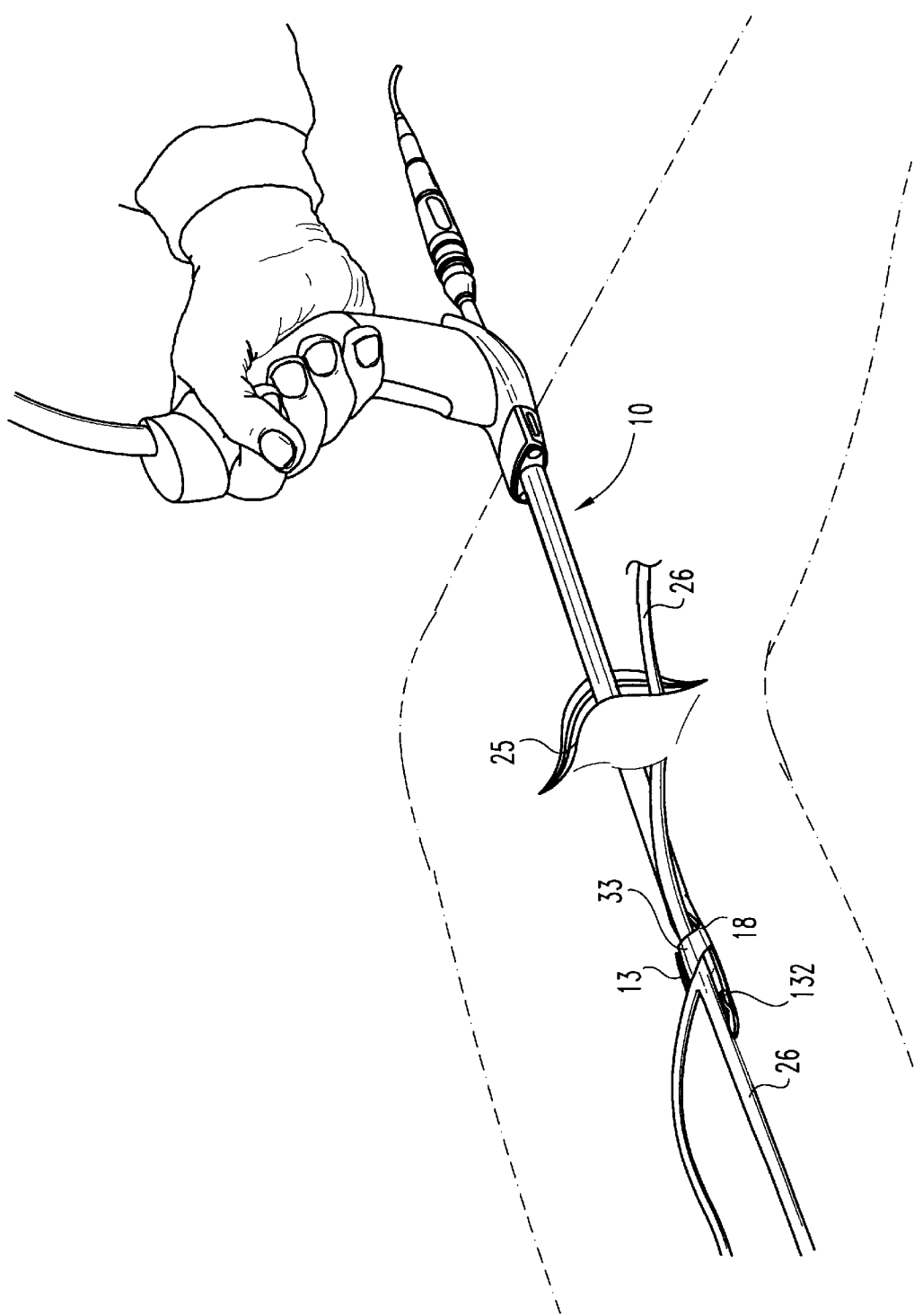
FIG. 29 is a perspective view showing the insertion of the dissecting device to a point at which a side branch is encountered.

As a further feature of the present invention, the shaft 11 may include one or more lumens extending the length thereof. Alternative designs are shown in FIGS. 25 and 26. The dissecting device 60 of FIG. 25 includes a single lumen 61 having an arcuate shape. Clip applies and various other devices 62 may be extended through the lumen 61 and positioned as desired for use adjacent to the dissecting tip. In the alternative design of FIG. 26, the shaft is provided with a plurality of lumens 63 extending the length of the shaft which allow one or more devices 62 to be extended therethrough to selected locations relative to the dissecting tip.

For any of the foregoing devices, the various light sources and retaining features may be included in the full range of possible combinations, as desired for the intended use of the device. For example, the dissecting tip may include only the distal trough and upwardly extending arms, with or without a light source. Alternatively, the dissecting tip may include only the upstanding tabs, or the tabs in combination with the upwardly extending arms. The full range of combinations of design elements are contemplated as a part of the present invention.

The components of the described devices and attendant features may be provided in a similar wide range of specific designs and materials. The dissecting tip and shaft are formed of suitable biocompatible material of types well known in the art. The dissecting tip may be configured to be permanently affixed to the shaft, or may be separable from the shaft such as by a threaded coupling. In use, the entire device or only certain parts, typically the dissecting tip and shaft, may he disposable.

The foregoing devices are useful in performing visualization, dissection and/or harvesting of vessels of the body. Embodiments which do not include lighting means are equally useful and advantageous for purposes of dissecting, and potentially harvesting, vessels. Although not limited in this respect, preferred methods of the present invention will be further described in respect to the exemplary use with respect to the saphenous vein. The following description is directed to a dissecting device with lighting means, but it will be appreciated that such method is directly suitable for use without transillumination in moving the device relative to the selected vessel.

A minimally-invasive surgical procedure is exemplified in the FIGS. 27–30. In accordance with a typical procedure, a vessel is dissected from surrounding tissue within the body of the person. An incision 25 is made in the body adjacent the vessel 26 and a dissecting device 10 is inserted into the person through the incision. The dissecting device includes a shallow, concave dissecting tip 13 having retaining structures for assisting in retaining the dissecting tip in position with respect to the vessel as the tip is advanced relative to the vessel.

The dissecting tip 13 is positioned with the vessel 26 received by the retaining structures of the tip and the tip is then advanced along the vessel. In this process, the retaining structures operate to retain the dissecting tip in position relative to the vessel to cause dissection of the vessel from the surrounding tissue.

As the dissecting tip 13 is advanced, the associated retaining structures and dissecting surfaces will act in the manner previously described. For example, as the tip is moved forward the vessel 26 is received within and retained by the provided retaining structures, which may include any or all of a trough 127 in the distal end of the tip, upwardly extending tabs 132 at the distal end of the tip, and arms 33 extending upwardly from the tip at a position displaced from the distal end of the tip.

Also, the confronting edges or surfaces of these various design features of the tip will contact the surrounding tissue and/or side branches. As the device is pushed forward through the body, as depicted successively in FIGS. 27–30, side branches ride up over and/or are transected by the front tabs. The front edges of the arms, including notches when provided, will transect any side branches and dissect the vessel from any adjoining tissue which is engaged by such edges.

If the vessel is to be harvested, then additionally the vessel is transected at selected proximal and distal locations and the separated vessel is removed. Transection of the vessel will typically be accomplished through incisions made in the body adjacent the desired proximal and distal locations of the vessel.

While the invention has been illustrated and described in detail in the drawings and foregoing description, the same is to be considered as illustrative and not restrictive in character, it being understood that only the preferred embodiment has been shown and described and that all changes and modifications that come within the spirit of the invention are desired to be protected.

What is claimed is:

1. A device useful for minimally-invasive surgical procedures involving a vessel of the body, said device comprising:

a shaft having a proximal end and a distal end;

a handle attached to the proximal end of said shaft;

a tip attached to the distal end of said shaft; and a light source mounted adjacent said tip and directing light laterally of said tip;

wherein said tip includes retaining structures for assisting in retaining said tip in position adjacent the vessel; and, wherein said retaining structures include a pair of tabs extending upwardly at the distal end of said tip for reception of the vessel therebetween.

2. A device useful for minimally-invasive surgical procedures involving a vessel of the body, said device comprising:

a shaft having a proximal end and a distal end;

a handle attached to the proximal end of said shaft;

a tip attached to the distal end of said shaft; and a light source mounted adjacent said tip and directing light laterally of said tip;

wherein said tip includes retaining structures for assisting in retaining said tip in position adjacent the vessel; and, wherein said retaining structures includes a pair of arms extending upwardly from said tip at a location displaced from the distal end of said tip, the pair of arms defining a confinement space for reception of the vessel therein.

3. The device of claim 2 in which said retaining structures includes a trough formed in the distal end of said tip for reception of the vessel therein.

4. The device of claim 2 in which said retaining structures further includes a pair of tabs extending upwardly at the distal end of said tip for reception of the vessel therebetween.

5. A dissection device useful for minimally-invasive surgical procedures involving a vessel of the body, said device comprising:

a shaft having a proximal end and a distal end;

a handle attached to the proximal end of said shaft; and a shallow, concave tip attached to the distal end of said shaft, said tip including retaining structures for retaining the vessel adjacent said tip as said tip is moved along the vessel:

wherein the retaining structures include a trough formed in the distal end of said tip for reception of a vessel therein; and wherein said tip includes a sharp front edge of the trough.

6. A dissection device useful for minimally-invasive surgical procedures involving a vessel of the body, said device comprising:

a shaft having a proximal end and a distal end;

a handle attached to the proximal end of said shaft; and a shallow, concave tip attached to the distal end of said shaft, said tip including retaining structures for retaining the vessel adjacent said tip as said tip is moved along the vessel; and, wherein the retaining structures include a pair of tabs extending upwardly at the distal end of said tip for reception of a vessel therebetween.

7. The device of claim 6 in which the tabs include sharp upper edges.

8. The device of claim 6 and which further includes a trough formed in the distal end of said tip for reception of a vessel therein.

9. A dissection device useful for minimally-invasive surgical procedures involving a vessel of the body, said device comprising:

a shaft having a proximal end and a distal end;

a handle attached to the proximal end of said shaft; and a shallow, concave tip attached to the distal end of said shaft, said tip including retaining structures for retaining the vessel adjacent said tip as said tip is moved along the vessel; and, wherein the retaining structures include a pair of arms extending upwardly from said tip at a location displaced from the distal end of said tip, the pair of arms defining a confinement space for reception of a vessel therein.

10. The device of claim 9 in which said arms extend up and abut with one another to define a closed space in which the vessel is received.

11. The dissecting device of claim 10 in which said shaft includes a central lumen extending therethrough.

12. The dissecting device of claim 10 in which said tip includes cautery means for cauterizing tissue adjacent the tip.

13. The device of claim 10 in which the arms include front edges which define sharp notches within which side branches of a vessel are receivable.

14. The device of claim 10 in which the arms extend upwardly and toward each other, the arms terminating in ends which are mutually-facing and are spaced apart from one another a distance sufficient to receive a vessel therebetween.

15. The device of claim 10 in which the arms extend upwardly and toward each other, the arms terminating in ends which are overlapping one over the other and are spaced apart from one another a distance sufficient to receive a vessel therebetween.

16. The device of claim 10 in which the arms extend upwardly and toward each other, the arms terminating in ends which are mutually-facing and which abut one another.

17. The device of claim 16 in which the arms are sufficiently flexible to permit displacement of the ends away from each other a sufficient distance to permit a vessel to be received therebetween.

18. The device of claim 10 in which said arms define an S-shaped slot therebetween.

19. The device of claim 10 in which the retaining structures further include a trough formed in the distal end of said tip for reception of a vessel therein.

20. The device of claim 10 in which the retaining structures further include a pair of tabs extending upwardly at the distal end of said tip for reception of a vessel therein.

21. The device of claim 20 in which the retaining structures include a trough formed in the distal end of said tip for reception of a vessel therein.

22. The device of claim 9 in which the arms include sharp front edges.

23. A dissection tip useful for minimally-invasive surgical procedures involving a vessel of the body, said tip comprising:

a shallow concave body including retaining structures for assisting in retaining said tip in position adjacent a vessel as said tip is advanced along the vessel;

wherein the retaining structures include a trough formed in the distal end of said tip for reception of a vessel therein; and, wherein the trough includes a sharp front edge.

24. A dissection tip useful for minimally-invasive surgical procedures involving a vessel of the body, said tip comprising:

a shallow concave body including retaining structures for assisting in retaining said tip in position adjacent a vessel as said tip is advanced along the vessel; and, wherein the retaining structures include a pair of tabs extending upwardly from said tip at the distal end of said tip for reception of a vessel therebetween.

25. The tip of claim 24 in which the tabs include sharp upper edges.

26. The tip of claim 24 and which further includes a trough formed in the distal end of said tip for reception of a vessel therein.

27. A dissection tip useful for minimally-invasive surgical procedures involving a vessel of the body, said tip comprising:

a shallow concave body including retaining structures for assisting in retaining said tip in position adjacent a vessel as said tip is advanced along the vessel; and, wherein the retaining structures include a pair of arms extending upwardly from said tip at a location displaced from the distal end of said tip, the pair of arms defining a confinement space for reception of a vessel therein.

28. The device of claim 27 in which the arms include sharp front edges.

29. The device of claim 27 in which the arms include front edges which define notches within which side branches of a vessel are receivable.

30. The device of claim 27 in which the arms extend upwardly and toward each other, the arms terminating in ends which are mutually-facing and are spaced apart from one another a distance sufficient to receive a vessel therebetween.

31. The device of claim 27 in which the arms extend upwardly and toward each other, the arms terminating in ends which are overlapping one over the other and are spaced apart from one another a distance sufficient to receive a vessel therebetween.

32. The device of claim 27 in which the arms extend upwardly and toward each other, the arms terminating in ends which are mutually-facing and which abut one another.

33. The device of claim 27 in which the arms are sufficiently flexible and spring loaded to permit displacement of the ends away from each other a sufficient distance to permit a vessel to be received therebetween.

34. The device of claim 27 in which the retaining structures further include a trough formed in the distal end of said tip for reception of a vessel therein.

35. The device of claim 27 in which the retaining structures further include a pair of tabs extending upwardly from said tip at the distal end of said tip for reception of a vessel therebetween.

36. The device of claim 27 in which the retaining structures further include a trough formed in the distal end of said tip for reception of a vessel therein.

37. A method for dissecting a vessel from surrounding tissue within the body of a person using visualization of the vessel through the person's skin, which method comprises:

making an incision in the body adjacent the vessel;

inserting a dissecting device into the person through the incision, the dissecting device including a dissecting tip and a light source mounted adjacent the dissecting tip and directing light laterally;

positioning the dissecting tip and light source posterior of the vessel with light directed laterally outward in the direction of the vessel;

visualizing the vessel through the person's skin by means of the light source directing light past the vessel and through the person's skin;

advancing the dissecting device along the vessel by means of said visualizing of the vessel, the dissecting tip operating in said advancing to dissect the vessel from surrounding tissue; and, wherein the dissecting tip has a reflecting surface and the light source is positioned adjacent the reflecting surface of said dissecting tip to reflect therefrom.

38. A method for dissecting a vessel from surrounding tissue within the body of a person using visualization of the vessel through the person's skin, which method comprises:

making an incision in the body adjacent the vessel;

inserting a dissecting device into the person through the incision, the dissecting device including a dissecting tip and a light source mounted adjacent the dissecting tip and directing light laterally;

positioning the dissecting tip and light source posterior of the vessel with light directed laterally outward in the direction of the vessel;

visualizing the vessel through the person's skin by means of the light source directing light past the vessel and through the person's skin;

advancing the dissecting device along the vessel by means of said visualizing of the vessel, the dissecting tip operating in said advancing to dissect the vessel from surrounding tissue; and, wherein the dissecting tip includes retaining structures for retaining a vessel in position adjacent said tip, said method further comprising positioning the vessel within the retaining structures carried by the dissecting device for assisting in retaining the dissecting tip adjacent the vessel.

39. The method of claim 38 and which includes positioning the vessel within a trough formed in the distal end of the dissecting tip.

40. The method of claim 38 and which includes positioning the vessel between a pair of tabs extending upwardly from the dissecting tip at the distal end of the dissecting tip.

41. The method of claim 38 and which includes positioning the vessel within a confinement area defined between a pair of arms extending upwardly from the dissecting tip at a location displaced from the distal end of the dissecting tip.

42. The device of claim 41 in which the arms extend upwardly and toward each other, the arms terminating in ends which are mutually-facing and are spaced apart from one another a distance sufficient to receive a vessel therebetween.

43. The device of claim 42 in which said arms define an S-shaped slot therebetween.

44. The device of claim 41 in which the arms extend upwardly and toward each other, the arms terminating in ends which are overlapping one over the other and are spaced apart from one another a distance sufficient to receive a vessel therebetween.

45. The device of claim 41 in which the arms extend upwardly and toward each other, the arms terminating in ends which are mutually-facing and which abut one another.

46. The device of claim 41 in which the arms are sufficiently flexible to permit displacement of the ends away from each other a sufficient distance to permit a vessel to be received therebetween.

47. The method of claim 41 and which includes positioning the vessel within a trough formed in the distal end of the dissecting tip.

48. The method of claim 41 and which includes positioning the vessel between a pair of tabs extending upwardly from the dissecting tip at the distal end of the dissecting tip.

49. A method for harvesting a vessel from within the body of a person using visualization of the vessel through the person's skin, which comprises:

making an incision in the body adjacent the vessel;

inserting a dissecting device into the person through the incision, the dissecting device including a dissecting tip and a light source mounted adjacent the dissecting tip and directing light laterally;

positioning the dissecting tip and light source posterior of the vessel with light directed outwardly in the direction of the vessel;

visualizing the vessel through the person's skin by means of the light source directing light past the vein and through the person's skin;

advancing the dissecting device along the vessel by means of said visualizing of the vessel, the dissecting tip operating in said advancing to dissect the vessel from surrounding tissue;

transecting the vessel at proximal and distal locations;

removing the vessel from the body; and, wherein the dissecting tip has a reflecting surface and the light source is positioned adjacent the reflecting surface of said dissecting tip to reflect therefrom.

50. A method for harvesting a vessel from within the body of a person using visualization of the vessel through the person's skin, which comprises:

making an incision in the body adjacent the vessel;

inserting a dissecting device into the person through the incision, the dissecting device including a dissecting tip and a light source mounted adjacent the dissecting tip and directing light laterally, positioning the dissecting tip and light source posterior of the vessel with light directed outwardly in the direction of the vessel;

visualizing the vessel through the person's skin by means of the light source directing light past the vein and through the person's skin;

advancing the dissecting device along the vessel by means of said visualizing of the vessel, the dissecting tip operating in said advancing to dissect the vessel from surrounding tissue;

transecting the vessel at proximal and distal locations;

removing the vessel from the body; and, positioning the vessel within retaining structures carried by the dissecting device for assisting in retaining the dissecting tip along the vessel.

51. A method for dissecting a vessel from surrounding tissue within the body of a person which comprises:

making an incision in the body adjacent the vessel;

inserting a dissecting device into the person through the incision, the dissecting device including a shallow, concave dissecting tip having retaining structures for assisting in retaining the dissecting tip in position with respect to the vessel as the tip is advanced relative to the vessel;

positioning the dissecting tip with the vessel received by the retaining structures of said tip; and advancing the dissecting tip along the vessel, the retaining structures of the dissecting tip operating in said advancing to retain the dissecting tip in position relative to the vessel to cause dissection of the vessel from surrounding tissue.

52. The method of claim 51 which includes positioning the vessel within a trough formed in the distal end of the dissecting tip.

53. The method of claim 51 which includes positioning the vessel between a pair of tabs extending upwardly at the distal end of the dissecting tip.

54. The method of claim 51 which includes positioning the vessel within a confinement area defined between a pair of arms extending upwardly from the dissecting tip at a location displaced from the distal end of the dissecting tip.

55. The method of claim 54 which further includes positioning the vessel within a trough formed in the distal end of the dissecting tip.

56. The method of claim 54 which further includes positioning the vessel between a pair of tabs extending upwardly at the distal end of the dissecting tip.

57. The method of claim 51 in which the vessel is a vein.

58. The method of claim 57 in which the vein is the saphenous vein.

59. A method for harvesting a vessel from within the body of a person which comprises:

making an incision in the body adjacent the vessel;

inserting a dissecting device into the person through the incision, the dissecting device including a shallow, concave dissecting tip having retaining structures for assisting in retaining the dissecting tip in position with respect to the vessel as the tip is advanced relative to the vessel;

positioning the dissecting tip with the vessel received by the retaining structures of said tip;

advancing the dissecting tip along the vessel, the retaining structures of the dissecting tip operating in said advancing to retain the dissecting tip in position relative to the vessel to cause dissection of the vessel from surrounding tissue;

transecting the vessel at proximal and distal locations; and removing the vessel from the body.

60. The method of claim 59 and which further includes transecting at least one side branch of the vessel.

61. The method of claim 59 and which further includes ligating and transecting at least one side branch of the vessel.

62. The method of claim 59 and which further includes cauterizing at least one side branch of the vessel.

63. The method of claim 59 in which the vessel is a vein.

64. The method of claim 63 in which the vein is the saphenous vein.

* * * * *